(12) United States Patent
Knoll et al.

(10) Patent No.: US 7,569,367 B2
(45) Date of Patent: Aug. 4, 2009

(54) NUCLEIC ACID PREPARATION FROM WHOLE BLOOD FOR USE IN DIAGNOSIS OF TRANSMISSIBLE SPONGIFORM ENCEPHALOPATHY

(75) Inventors: Michael Knoll, Penzberg (DE); Walter Eberle, Bernried (DE); Thomas Kirschbaum, Iffeldorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 8 days.

(21) Appl. No.: 11/514,776

(22) Filed: Sep. 1, 2006

(65) Prior Publication Data

US 2007/0065853 A1 Mar. 22, 2007

(30) Foreign Application Priority Data

Sep. 7, 2005 (EP) .................. 05019479

(51) Int. Cl.
*C12P 19/34* (2006.01)
*C12Q 1/68* (2006.01)
(52) U.S. Cl. .......................... 435/91.2; 435/6
(58) Field of Classification Search ............. 435/91.2
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 4,996,143 A | 2/1991 | Heller et al. | |
| 5,118,801 A | 6/1992 | Lizardi et al. | |
| 5,386,024 A | 1/1995 | Kacian et al. | |
| 5,565,322 A | 10/1996 | Heller | |
| 5,849,489 A | 12/1998 | Heller | |
| 5,863,742 A | 1/1999 | Oh et al. | |
| 6,162,603 A | 12/2000 | Heller | |
| 2002/0146677 A1* | 10/2002 | Augello et al. | 435/2 |

FOREIGN PATENT DOCUMENTS

| | | |
|---|---|---|
| WO | WO 84/03285 | 8/1984 |
| WO | WO 90/04237 | 4/1990 |
| WO | WO 91/12079 | 8/1991 |
| WO | WO 97/46707 | 12/1997 |
| WO | WO 97/46712 | 12/1997 |
| WO | WO 97/46714 | 12/1997 |
| WO | WO 98/04730 | 2/1998 |
| WO | WO 99/46403 | 6/1999 |
| WO | WO 01/37291 A1 | 5/2001 |
| WO | WO 02/074986 | 9/2002 |
| WO | WO 2004/005098 A1 | 6/2004 |
| WO | WO 2005/042784 A2 | 5/2005 |
| WO | WO 2005/049863 A2 | 6/2005 |

OTHER PUBLICATIONS

Smith et al. Genome Research, vol. 11, No. 4, pp. 636-630, 2001.*
Bhudevi et al. Veterinary Microbiology, vol. 83, pp. 1-10, 2001.*
QIAGEN, QIAamp RNA Blood Mini Handbook, http://www.qiagen,com, Jan. 1999.*
Alderton, R. et al., "Magnetic Bead Purification of M13 DNA Sequencing Templates," Analytical Biochemistry 201, 166-169 (1992).
Bernard, P. et al., "Integrated Amplification and Detection of the C677T Point Mutation in the Methylenetetrahydrofolate Reductase Gene by Fluorescence Resonance Energy Transfer and Probe Melting Curves," Analytical Biochemistry 255, 101-107 (1998).
Lu, Z. et al., "New Molecular Markers of Early and Progressive CJD Brain Infection," Journal of Cellular Biochemistry 93:644-652(2004).
Schweighoffer, F. et al., Qualitative Gene Profiling: A Novel Tool in Genomics and in Pharmacogenomics that Deciphers Messenger RNA Isoforms Diversity, Pharmacogenomics (2000) 1(2):187-197.
Walsh, C., Enzymatic Reaction Mechanisms, W.H. Freeman and Company, 1979, Chapter 3, p. 53-107.
Wittwer, C. et al., "Continuous Fluorescence Monitoring of Rapid Cycle DNA Amplifications," BioTechniques 22: 130-138(Jan. 1997).

* cited by examiner

*Primary Examiner*—Gary Benzion
*Assistant Examiner*—Cynthia B Wilder
(74) *Attorney, Agent, or Firm*—Marilyn Amick

(57) ABSTRACT

The present invention deals with a method of preparing nucleic acids, particularly RNA, from a whole blood sample. The nucleic acids purified by the method of the invention are particularly suited for detection of nucleic acid marker molecules. Preferred are markers for the diagnosis of transmissible spongiform encephalopathy (TSE). Such diagnosis is based on the detection, by means of real-time PCR, of certain mRNAs of the TSE-infected organism. Said mRNAs specifically originate as splicing variants and are isolated from whole blood by the method of the invention.

14 Claims, 13 Drawing Sheets

| animal no. | animal status | RNA yield ng/µl |
|---|---|---|
| H-1 | "H"=healthy | 10,25 |
| H-2 | "H"=healthy | 3,53 |
| H-3 | "H"=healthy | 3,22 |
| H-4 | "H"=healthy | 4,11 |
| H-5 | "H"=healthy | 5,09 |
| H-6 | "H"=healthy | 2,41 |
| H-7 | "H"=healthy | 2,75 |
| H-8 | "H"=healthy | 5,74 |
| H-9 | "H"=healthy | 6,46 |
| H-10 | "H"=healthy | 4,30 |
| H-11 | "H"=healthy | 4,50 |
| H-12 | "H"=healthy | 3,41 |
| H-13 | "H"=healthy | 10,73 |
| H-14 | "H"=healthy | 7,91 |
| H-15 | "H"=healthy | 7,69 |

B

| animal no. | animal status | RNA yield ng/µl |
|---|---|---|
| NI-1 | "NI"=naturally inf. | 4,04 |
| NI-2 | "NI"=naturally inf. | 3,01 |
| NI-3 | "NI"=naturally inf. | 1,94 |
| NI-4 | "NI"=naturally inf. | 3,30 |
| NI-5 | "NI"=naturally inf. | 4,82 |
| NI-6 | "NI"=naturally inf. | 3,40 |
| NI-7 | "NI"=naturally inf. | 2,80 |
| NI-8 | "NI"=naturally inf. | 1,99 |
| NI-9 | "NI"=naturally inf. | 3,21 |
| NI-10 | "NI"=naturally inf. | 2,62 |
| EI-1 | "EI"=experim. inf. | 4,29 |
| EI-2 | "EI"=experim. inf. | 4,25 |
| EI-3 | "EI"=experim. inf. | 3,59 |
| EI-4 | "EI"=experim. inf. | 3,77 |
| EI-5 | "EI"=experim. inf. | 2,72 |

Figure 4

| Program: | Reverse Transkription | | | | Type: | None | Cycles: | 1 |
|---|---|---|---|---|---|---|---|---|
| Segment Number | Temperature Target (°C) | Hold Time (sec) | Slope (°C/sec) | 2° Target Temp (°C) | Step Size (°C) | Step Delay (Cycles) | Acquisition Mode | |
| 1 | 61 | 1200 | 20 | 0 | 0 | 0 | None | |

| Program: | Denaturierung | | | | Type: | None | Cycles: | 1 |
|---|---|---|---|---|---|---|---|---|
| Segment Number | Temperature Target (°C) | Hold Time (sec) | Slope (°C/sec) | 2° Target Temp (°C) | Step Size (°C) | Step Delay (Cycles) | Acquisition Mode | |
| 1 | 95 | 30 | 20 | 0 | 0 | 0 | None | |

| Program: | Amplifikation | | | | Type: | Quantification | Cycles: | 34 |
|---|---|---|---|---|---|---|---|---|
| Segment Number | Temperature Target (°C) | Hold Time (sec) | Slope (°C/sec) | 2° Target Temp (°C) | Step Size (°C) | Step Delay (Cycles) | Acquisition Mode | |
| 1 | 95 | 10 | 20 | 0 | 0 | 0 | None | |
| 2 | 55 | 16 | 20 | 0 | 0 | 0 | Single | |
| 3 | 72 | 15 | 2 | 0 | 0 | 0 | None | |

| Program: | mc | | | | Type: | Melting Curves | Cycles: | 1 |
|---|---|---|---|---|---|---|---|---|
| Segment Number | Temperature Target (°C) | Hold Time (sec) | Slope (°C/sec) | 2° Target Temp (°C) | Step Size (°C) | Step Delay (Cycles) | Acquisition Mode | |
| 1 | 95 | 0 | 20 | 0 | 0 | 0 | None | |
| 2 | 40 | 30 | 20 | 0 | 0 | 0 | None | |
| 3 | 80 | 0 | 0.1 | 0 | 0 | 0 | Continuous | |

| Program: | cool | | | | Type: | None | Cycles: | 1 |
|---|---|---|---|---|---|---|---|---|
| Segment Number | Temperature Target (°C) | Hold Time (sec) | Slope (°C/sec) | 2° Target Temp (°C) | Step Size (°C) | Step Delay (Cycles) | Acquisition Mode | |
| 1 | 40 | 30 | 20 | 0 | 0 | 0 | None | |

NUCLEIC ACID PREPARATION FROM WHOLE BLOOD FOR USE IN DIAGNOSIS OF TRANSMISSIBLE SPONGIFORM ENCEPHALOPATHY

RELATED APPLICATIONS

This application claims priority to EP 05019479.4 filed Sep. 7, 2005.

FIELD OF THE INVENTION

The present invention deals with a method of preparing nucleic acids, particularly ribonucleic acid (RNA), from a whole blood sample. The nucleic acids purified by the method of the invention are particularly suited for detection of nucleic acid marker molecules. Preferred are markers for the diagnosis of transmissible spongiform encephalopathy (TSE). Such diagnosis is based on the detection, by means of real-time PCR, of certain mRNAs of the TSE-infected organism. Said mRNAs specifically originate as splicing variants and are isolated from whole blood by the method of the invention.

BACKGROUND OF THE INVENTION

Transmissible spongiform encephalopathies (TSEs) consist of a unique group of invariably fatal neurological disorders which affect both human and animals. TSEs are characterized by long presymptomatic incubation periods of months or years. Brain lesions associated with deposits of protease-resistant proteins are a hallmark of clinically manifest TSE disease.

Variant Creutzfeldt-Jakob disease (vCJD) is a rare and fatal human neurodegenerative condition. The classical form, that is to say CJD, presents as a subacute dementia, evolving over weeks to several months and is accompanied by pyramidal, extrapyramidal, and cerebellar signs. The mean age of death is 57 years but the disease may occur in the late teens and early twenties. In the final stages of the disease, there is an incapacitating dementia, usually with severe myoclonus. Recently, a variant of CJD (vCJD) was described in UK and France with distinct clinical and pathological features which affected younger individuals (average age 2-9 years, as opposed to 65 years).

As with CJD, vCJD is classified as a TSE because of characteristic spongy degeneration of the brain and its ability to be transmitted. The presumed infectious agent of TSE is often termed $PrP^{sc}$ or $PrP^{res}$ denoting the disease-specific form of the prion protein (PrP). The biological properties of $PrP^{sc}$ in vCJD and BSE share common biological properties e.g. they have similar incubation periods in various kinds of mice and hamsters. TSEs are also known in other animals. For instance, scrapie affects sheep and goats and has been found in many sheep-producing countries throughout the world for over 50 years. Chronic Wasting Disease (CWD) is a contagious fatal TSE in cervids (members of the deer and elk family).

The hypothesis of a link between vCJD and BSE was first raised because of the association of these two TSEs in time and place. More recent evidence supporting a link including identification of pathological features similar to vCJD in brains of macaque monkeys inoculated with BSE. A vCJD-BSE link is further supported by the demonstration that vCJD is associated with a molecular marker that distinguishes it from other forms of CJD and which resembles that seen in BSE transmitted to a number of other species. Studies of the distribution of the infectious agent in the brains of mice artificially infected with tissues from humans with vCJD and cows with BSE showed nearly identical patterns. The most recent and powerful evidence comes from studies showing that the transmission characteristics of BSE and vCJD in laboratory mice are almost identical, strongly indicating that they are due to the same causative agent. In conclusion, the most likely cause of vCJD is exposure to the BSE agent, most plausibly due to dietary contamination by affected bovine central nervous system tissue.

It follows that with regard to the human food chain there is an urgent need for methods to assess a possible TSE infection in the living host. Particularly there is a desire to assess TSE in living animals at a pre-symptomatic stage and before the animals are slaughtered and processed to enter the human food chain. One way to assess TSE is commonly applied when testing slaughtered cattle routinely for bovine spongiform encephalopathy. A brain sample is derived from a sacrificed animal and the presence of $PrP^{sc}/PrP^{res}$ in the sample is assessed by means of an immunological test such as an ELISA or a Western blot. Apart from assays which target the TSE-associated form of the prion protein there are several approaches to assess TSE disease using surrogate markers. An example for surrogate markers are proteins other than PrP which are disclosed in WO 99/04237.

An alternative approach targets TSE disease specific changes of gene expression. Neurodegeneration in the brain is apparently closely linked with alterations among the RNA transcripts in nervous tissues. In addition, alterations in expression can be present in other body tissues as the proposed way of infection is thought to lead through the gut and the bloodstream to cross the blood brain barrier into the central nervous system. It has been found by the inventors that determination, that is to say qualitative or quantitative detection of a disease-specific target nucleic acid, requires a special kind of purification providing nucleic acids in high quality. Particularly, nucleic acid yield has to be high enough for detection of even very small amounts of target nucleic acid. In addition, degradation is to be minimized and high purity is desired.

Established products for nucleic acid purification which are commercially available include the MAGNA PURE instrument for which a variety of nucleic acid purification kits are on the market. In addition, stabilization reagents for biological samples are known to the art, e.g. the RNA/DNA stabilization reagent for blood/bone marrow distributed by Roche Diagnostics GmbH (Mannheim, Germany; Catalogue no. 11934317). With these means at hand, current methods appear to be suited for many routine purposes. However, the inventors noticed that the preparation of nucleic acids including high quality RNA from whole blood samples required optimization for particular detection purposes.

In view of nucleic acids as surrogate markers Begic, L. et al., Medicinski Arhiv (2002) 56(5-6):305-311 discussed differential analysis of transcripts with alternative splicing (DATAS), among other approaches, to identify RNAs as molecular markers to provide a tool for the diagnosis of TSE.

The DATAS method aims at identifying in a selected tissue or cell population one or more disease-specific RNAs in the form of a splicing variant. Thus, the presence or absence of the splicing variant in the tissue or cell population is correlated with the diagnosis of TSE. Ideally, the occurrence of the splicing variant is restricted to TSE infected individuals. However, other experimental settings based on quantitative determination of a splicing variant are also possible. In the latter case the presence of the splicing variant at either a higher or a lower level in the tissue or cell population is taken as an indicator of TSE infection.

Using the DATAS method as described in WO 99/46403 a number of marker nucleotide sequences were disclosed in WO 02/074986. Marker sequences were obtained using experimentally infected mice and scrapie infected sheep. Another marker nucleotide sequence identified likewise by means of the DATAS method is disclosed in WO 2004/050908. In both cases the marker sequence was validated using a panel of blood samples from BSE-infected cattle. Methods to probe for marker sequences included Northern hybridization, deoxyribonucleic acid (DNA) microarray hybridization, and quantitative PCR.

WO 2005/049863 discloses further nucleic acid sequences as diagnostic markers in the assessment of subacute spongiform encephalopathies from biological samples. As previously, the sequences have been identified in blood cells using the DATAS method. In order to evaluate the particular usefulness of these sequences the inventors set out to establish an assay aimed at the requirements of routine use and enhanced sample throughput. To this end, it was an object of the invention to provide an optimized workflow for sampling and sample preparation, specific oligonucleotide primer pairs for amplification of the marker nucleotide sequences by means of the polymerase chain reaction (PCR), and the detection of specific amplification products. It was another object of the invention to set up a PCR assay format which provides for a quick and reliable outcome of the diagnostic assay. Further, it was an object of the invention, to optimize test performance.

SUMMARY OF THE INVENTION

The invention provides methods of purifying particularly high amounts of intact and pure nucleic acids from whole blood samples. These methods pave the way for assessing TSE in a whole blood sample by detecting disease-specific differentially spliced transcripts. Primers and probes for detecting TSE are provided by the invention, as are kits containing such primers and probes. Methods of the invention can be used to rapidly identify TSE-infected cattle. In a particularly preferred embodiment using specific primers and probes, the methods include amplifying and monitoring the development of specific amplification products.

A first aspect of the invention is a method for purifying nucleic acids from a whole blood sample, comprising the steps of (a) providing a whole blood sample from a mammal, whereby the sample is not older than 5 minutes; (b) subsequently mixing the sample with anticoagulant; (c) mixing the composition of (b) with an aequous stabilization reagent comprising a non-ionic detergent and a guanidinium salt, whereby the final concentration of the guanidinium salt in the resulting mixture is between 15% and 35% weight by volume, and the final concentration of the non-ionic detergent in the resulting mixture is between 3% and 10% volume by volume; (d) incubating the composition of (c) for about 10 minutes; (e) subsequently shock-freezing the composition, thereby solidifying the composition homogeneously; (f) optionally storing the composition of step (e) in a frozen, solidified state; (g) thawing the frozen composition of step (e) in the presence of an aequous lysis reagent comprising a guanidinium salt, whereby the volume of the lysis buffer adjusts the final concentration of the guanidinium salt in the resulting mixture after thawing to a concentration of between 3.5 M and 4.2 M; (h) adsorbing the nucleic acids contained in the composition of step (g) (liquid phase) to a solid phase, separating the solid phase from the liquid phase, optionally washing the solid phase with the adsorbed nucleic acids and subsequently desorbing the nucleic acids from the solid phase with an elution buffer, thereby purifying said nucleic acids.

Another aspect of the invention is a composition comprising whole blood, an anticoagulant, a guanidinium salt, and a non-ionic detergent, in a frozen and homogeneously solid state of aggregation. The composition preferably further includes water and optionally a buffer salt. Also preferred, the composition is a homogeneous mixture of said components. With regard to the state of aggregation the term "frozen and homogeneously solid" means that the composition is essentially free of any residual liquid phase. A frozen and homogeneously solid state of aggregation of said composition is preferably prepared by snap-freezing in liquid nitrogen. Thus another preferred embodiment of the invention is a composition comprising whole blood, an anticoagulant, a guanidinium salt, and a non-ionic detergent, in a homogeneously solid state of aggregation, obtainable by freezing said composition in liquid nitrogen.

A further aspect of the invention is a method of determining the presence of a target nucleic acid in a whole blood sample, comprising the steps of (a) purifying nucleic acids from the whole blood sample according to the method for purifying nucleic acids according to the invention; (b) detecting among the purified nucleic acids of step (a) the presence of the target nucleic acid, thereby determining the presence of the target nucleic acid. A particularly preferred embodiment step (b) is a method comprising the steps of performing at least one cycling step, wherein a cycling step comprises an amplifying step and hybridizing step, wherein said amplifying step comprises contacting said sample with a pair of LT1, LT3 or LT4 primers to produce LT1, LT3 or LT4 amplification product if a target nucleic acid LT1 (SEQ ID NO:1), LT3 (SEQ ID NO:6), or LT4 (SEQ ID NO:11) is present in said sample, wherein said hybridizing step comprises contacting said sample with a pair of LT1, LT3 or LT4 probes, wherein the members of said pair of LT1, LT3 or LT4 probes hybridize within no more than five nucleotides of each other, wherein a first LT1, LT3 or LT4 probe of said pair of LT1, LT3 or LT4 probes is labelled with a donor fluorescent moiety and said second LT1, LT3 or LT4 probe of said pair of LT1, LT3 or LT4 probes is labelled with a corresponding acceptor fluorescent moiety; and detecting the presence or absence of fluorescence resonance energy transfer (FRET) between said donor fluorescent moiety of said first LT1, LT3 or LT4 probe and said acceptor fluorescent moiety of said second LT1, LT3 or LT4 probe, wherein the presence of FRET is indicative of the presence of transmissible spongiform encephalopathy (TSE) in the individual from which said sample, derives and wherein the absence of FRET in indicative of the absence of TSE in said individual.

In some aspects, one of the LT1, LT3, or LT4 primers can be labeled with a fluorescent moiety (either a donor or acceptor, as appropriate) and can take the place of the LT1, LT3, or LT4 probes, respectively.

The members of the pair of LT1, LT3, or LT4 probes can hybridize within no more than two nucleotides of each other, or can hybridize within no more than one nucleotide of each other. A representative donor fluorescent moiety is fluorescein, and corresponding acceptor fluorescent moieties include LC-Red 640, LC-Red 705, Cy5, and Cy5.5. Additional corresponding donor and acceptor fluorescent moieties are known in the art.

In one aspect, the detecting step includes exciting the sample at a wavelength absorbed by the donor fluorescent moiety and visualizing and/or measuring the wavelength emitted by the acceptor fluorescent moiety (i.e., visualizing and/or measuring FRET). In another aspect, the detecting step includes quantitating the FRET. In yet another aspect, the detecting step can be performed after each cycling step (e.g., in real-time).

Generally, the presence of FRET within 45 cycles (e.g. 20, 25, 30, 35, or 40 cycles) indicates the presence of SEQ ID NOs:1, 6 or 11 in the blood sample, depending on which of the LT1, LT3, or LT4 primers and probes are used. In addition, determining the melting temperature between one or both of the LT1 probe(s) and the LT1 amplification product or, similarly, between one or both of the LT3 or LT4 probe(s) and the LT3 or LT4 amplification product, respectively, can confirm the presence or absence of the respective sequence, that is SEQ ID NO:1, SEQ ID NO:6 or SEQ ID NO:11.

In addition, the cycling step can be performed on a control sample. A control sample can include two control plasmids, one with the respective splicing marker, the second one without this marker or a mixture of both in a suitable ratio or nucleic acid preparations of BSE-infected and non-infected cattle. Cycling steps can be performed on such a control sample using a pair of control primers and a pair of control probes. The control primers and probes are other than primers and probes used in the respective detection experiment. One or more amplifying steps produces a control amplification product. Each of the control probes hybridizes to the control amplification product.

In another aspect of the invention, there are provided articles of manufacture, or kits. Kits of the invention can include a pair of LT1 primers according to SEQ ID NO:2. and SEQ ID NO:3. Preferably, a kit according to the invention further includes the oligonucleotides according to SEQ ID NO:4 and SEQ ID NO:5. It is preferred that a kit further includes a pair of LT3 primers according to SEQ ID NO:7 and SEQ ID NO:8 and, more preferred in addition the oligonucleotides according to SEQ ID NO:9 and SEQ ID NO:10. It is also preferred that a kit further includes a pair of LT4 primers according to SEQ ID NO:12 and SEQ ID NO:13 and, more preferred in addition the oligonucleotides according to SEQ ID NO:14 and SEQ ID NO:15.

Kits can include fluorophoric moieties for labeling the probes or probes already labeled with donor and corresponding acceptor fluorescent moieties. The Kit can also include a package insert having instructions thereon for using the primers, probes, and fluorophoric moieties to detect the presence or absence of a marker sequence selected from the group consisting of LT1, LT3 and LT4 in a sample.

In yet another aspect of the invention, there is provided a method for assessing TSE in a bovine animal. Such a method includes performing at least one cycling step. A cycling step can include an amplifying step and a hybridizing step. Generally, an amplifying step includes contacting the sample with a pair of LT1 primers to produce a LT1 amplification product if a LT1 nucleic acid molecule is present in the sample. Generally, a hybridizing step includes contacting the sample with a LT1 probe. Such a LT1 probe is usually labeled with a donor fluorescent moiety and a corresponding acceptor fluorescent moiety. The method further includes detecting the presence or absence of fluorescence resonance energy transfer (FRET) between the donor fluorescent moiety and the acceptor fluorescent moiety of the LT1 probe. The presence or absence of fluorescence is indicative of TSE in said bovine animal. In addition to the LT1 primers/probe described herein, this method also can be performed using LT3 and/or LT4 primers/probe.

In one aspect, amplification can employ a polymerase enzyme having 5' to 3' exonuclease activity. Thus, the first and second fluorescent moieties would be within no more than 5 nucleotides of each other along the length of the probe. In another aspect, the LT1, LT3 or LT4 probe includes a nucleic acid sequence that permits secondary structure formation. Such secondary structure formation generally results in spatial proximity between the first and second fluorescent moiety. According to this method, the second fluorescent moiety on a probe can be a quencher.

In another aspect of the invention, there is provided a method for assessing TSE in a bovine animal. Such a method includes performing at least one cycling step. A cycling step can include an amplifying step and a dye-binding step. An amplifying step generally includes contacting the sample with a pair of LT1, LT3 or LT4 primers to produce a LT1, LT3 or LT4 amplification product if a LT1, LT3 or LT4 nucleic acid molecule is present in the sample. A dye-binding step generally includes contacting the LT1, LT3 or LT4 amplification product with a double-stranded DNA binding dye. The method further includes detecting the presence or absence of binding of the double-stranded DNA binding dye into the amplification product. According to the invention, the presence of binding is typically indicative of TSE in said bovine animal, and the absence of binding is typically indicative of the absence of TSE in said bovine animal. Such a method can further include the steps of determining the melting temperature between the LT1, LT3 or LT4 amplification product and the double-stranded DNA binding dye. Generally, the melting temperature confirms the presence or absence of LT1, LT3 or LT4. Representative double-stranded DNA binding dyes include SYBR Green I, SYBR Gold, and ethidium bromide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting.

(2) Thawing of samples: For thawing Dithiothreitol and MAGNA PURE lysis/binding buffer (Roche Diagnostics internal material no. 2 239 507) are added to frozen blood cell lysate of (1).

(3) RNA purification: Transfer of 900 µl of thawed and lysed blood into MAGNA PURE LC Instrument. Purification of total RNA with MAGNA PURE specific reagents and purification protocol. The total RNA is recovered in 100 µl elution buffer. Storage of RNA eluates at −80° C.

(4) Total RNA quality check: aliquots of total RNA preparations are run on an agarose gel stained with SYBR Green Gel Stain (Molecular Probes). Presence of 18S- and 28S-rRNA band and lack of smear, signals at running edge of gel is documenting high integrity (quality) of the respective total RNA preparation.

(5) Normalization of RNA amount: nucleic acid concentration of total RNA preparations are determined by Ribogreen RNA Quantification Kit (Molecular Probes).

The RNA concentration of all samples is adjusted to the same concentration by dilution with water.

(6) RT-PCR: Normalized RNA samples are templates for RT-PCR of the splicing markers LT1, LT3 and LT4 discriminating BSE infected and healthy individuals. Analysis of results is based on the crossing point of each individual sample.

Figure 2:
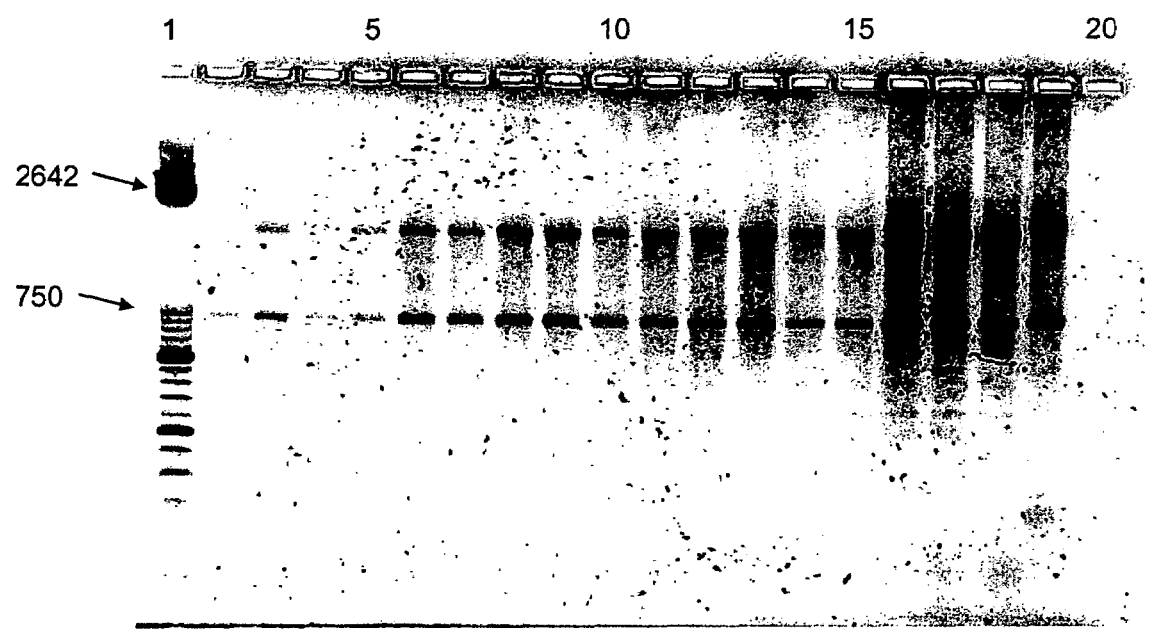

FIG. 2: Agarose gel showing integrity of total RNA samples of BSE-infected cattle and non-infected control animals. Size marker, fragment sizes in base pairs are indicated on the left. The gel was stained using SYBR Green Gel Stain (Molecular Probes).

Lane 1: DNA Molecular Weight Marker XIII (50-750 bp, Roche Diagnostics (catalogue no. 1 721 925). Mixture of restriction fragment sizes are 50, 100, 150, 200, 250, 500, 750 (black arrow), 2642 (black arrow).

Lane 2 to 5: duplicate of individual total RNA preparations of two BSE field cases (naturally BSE-infected, clinical, post-mortem BSE positive cases). Distinct bands correspond to 28S and 18S ribosomal RNAs.

Lane 6 to 15: duplicate of individual total RNA preparations of five experimentally BSE-infected cattle. Distinct bands correspond to 28S and 18S ribosomal RNAs.

Lane 16 to 18: triplicate of individual total RNA preparations of a non-infected individual. Distinct bands correspond to 28S and 18S ribosomal RNAs.

Lane 19: Isolate from HeLa cells (control). Distinct bands correspond to 28S and 18S ribosomal RNAs.

FIG. 3: RNA yield of individual bovine blood samples determined by RiboGreen RNA Quantification Kit (Molecular Probes catalogue no. R-11490).

A: non-infected cattle; B: infected cattle

FIG. 4: PCR conditions for amplification of markers LT1, LT3, and LT4.

Figure 5:
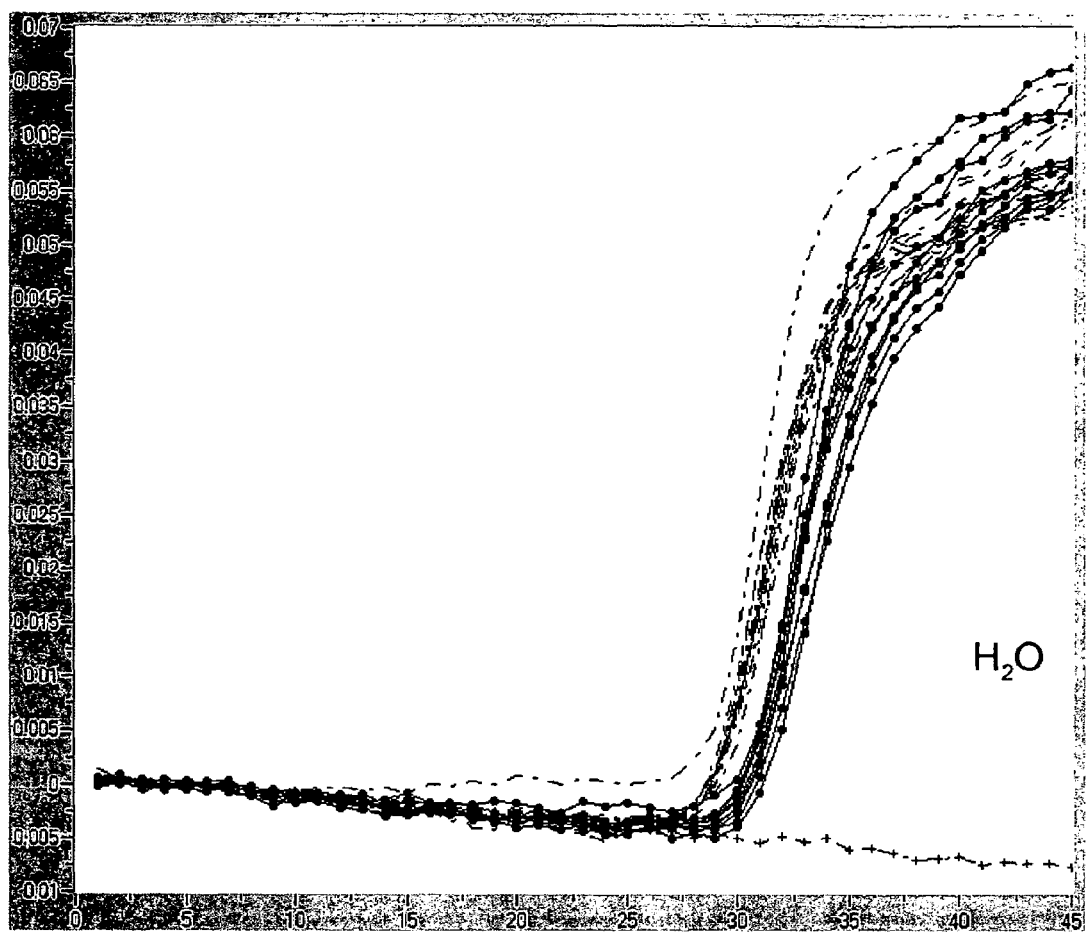

FIG. 5: LT1 amplification curves. Results from real-time RT-PCR of total RNA from whole blood samples of cattle using a LIGHTCYCLER instrument and the experimental setting as described in FIG. 4. Solid lines with circles indicate individual RT-PCR experiments with samples from BSE-infected animals, dotted lines indicate BSE-free animals. The Figure further illustrates the crossing point data given in Table 1. The ordinate indicates the values for fluorescence (F2/back-F1) as determined by the LIGHTCYCLER instrument, the abscissa indicates cycle numbers. The water control is marked by "$H_2O$".

Figure 6:
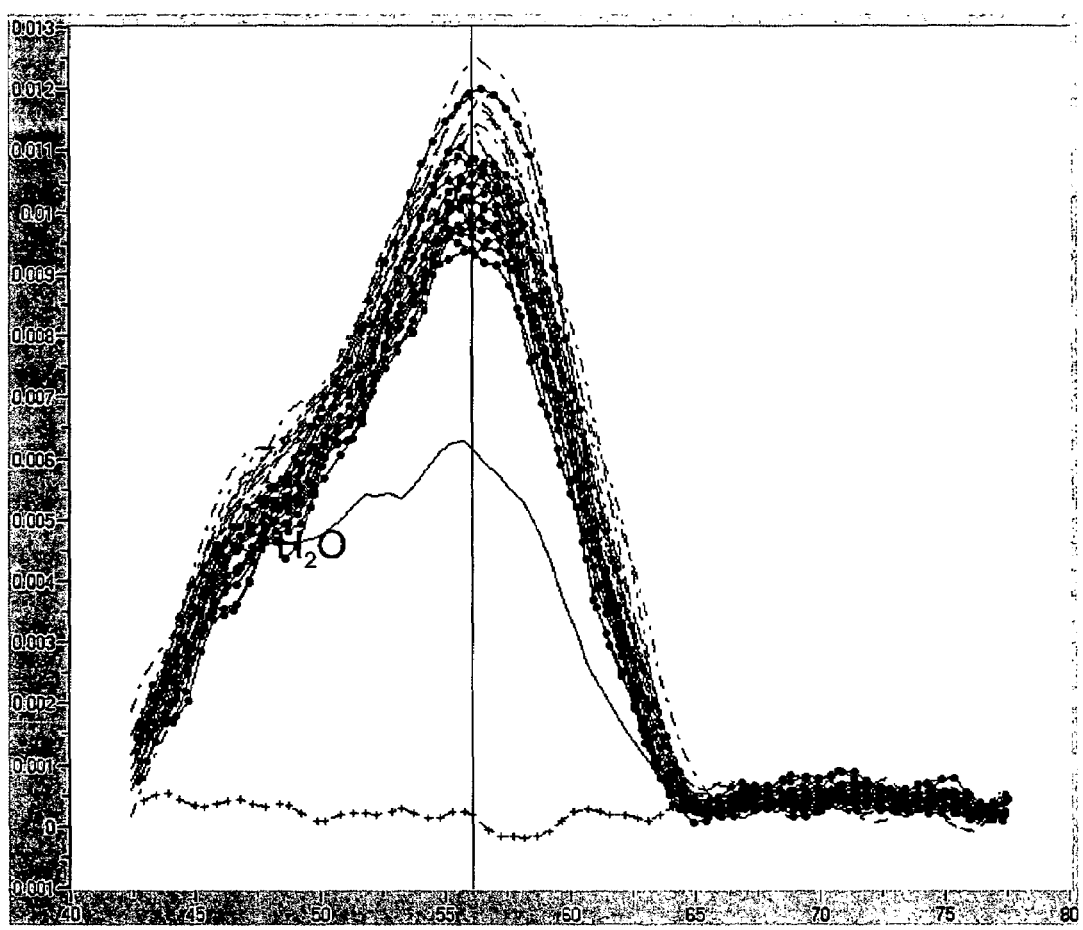

FIG. 6: LT1, melting curves. Results from melting curve analysis of total RNA from whole blood samples of cattle using a LIGHTCYCLER instrument and the experimental setting as described in FIG. 4. Solid lines with circles indicate individual RT-PCR experiments with samples from BSE-infected animals, dotted lines indicate BSE-free animals, solid line indicate control plasmid. As expected the Figure illustrates comparable melting curve shape and melting temperature for all samples. The ordinate indicates the values for fluorescence (F2/back-F1) as determined by the LIGHTCYCLER instrument, the abscissa indicates the reaction temperature. The water control is marked by "$H_2O$".

Figure 7:
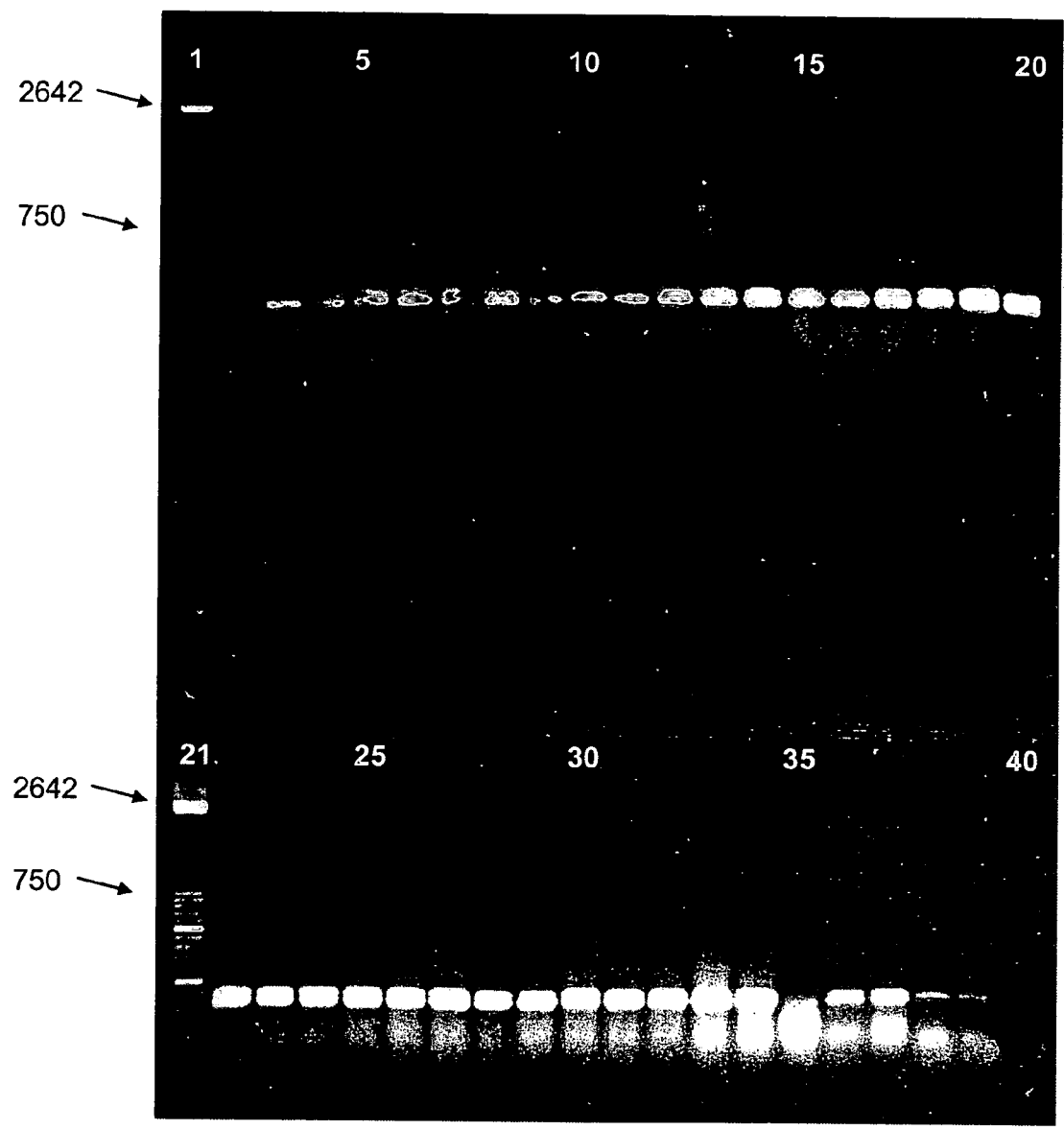

FIG. 7: LT1 Gel. Agarose gel showing RT-PCR product of amplification with LT1 primers from BSE-infected and non-infected control animals. Size marker, fragment sizes in base pairs are indicated on the left. The gel was stained using SYBR Green Gel Stain (Molecular Probes). RT-PCR products compared to marker DNA are of expected size (above 150 bp band; exact size: 161 bp).

By sequencing the LT1 RT-PCR product of biological samples showed a 100% nucleotide sequence identity with control plasmid and splicing marker sequence.

Further description of the samples:

Lane 1: DNA Molecular Weight Marker XIII (50-750 bp, Roche Diagnostics (catalogue no. 1 721 925). Mixture of restriction fragment sizes are 50, 100, 150, 200, 250, 500, 750 (black arrow), 2642 (black arrow).

Lane 2: water control (negative control).

Lane 3 to 17: RT-PCR products from samples of BSE-free animals.

Lane 18 to 20: RT-PCR products from samples of BSE-infected animals in the late stage of the disease (naturally infected, post-mortem positive).

Lane 21: DNA Molecular Weight Marker XIII (50-750 bp, Roche Diagnostics (catalogue no. 1 721 925). Mixture of restriction fragment sizes are 50, 100, 150, 200, 250, 500, 750 (black arrow), 2642 (black arrow).

Lane 22 to 28: RT-PCR products from samples of BSE-infected animals in the late stage of the disease (naturally infected, post-mortem positive).

Lane 29 to 33: RT-PCR products from samples of BSE-infected animals in the early stage of the disease (experimentally infected).

Lane 34: LT1 control plasmid (positive control).

Lane 35: water control (negative control).

Lane 36 to 39: samples of another experiment (not relevant for this analysis).

Figure 8:
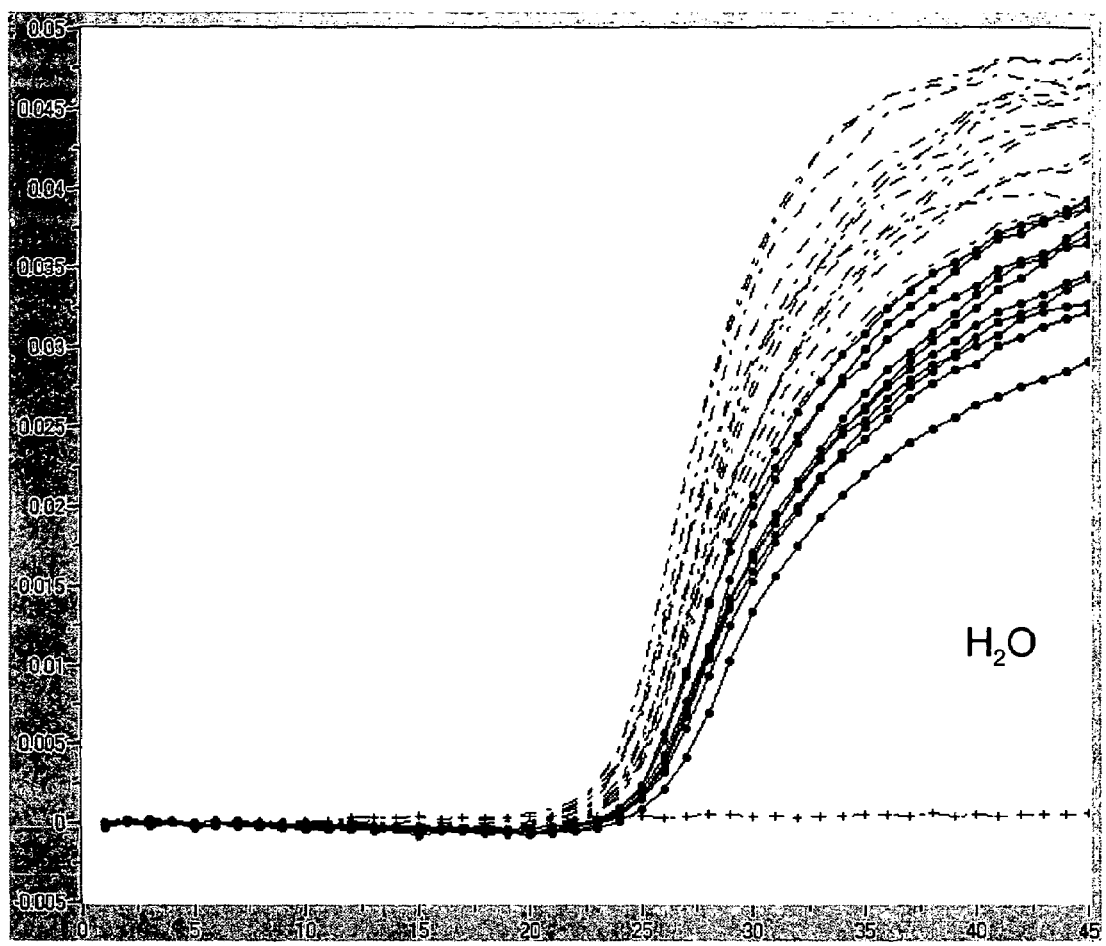

FIG. 8: LT3 amplification curves. Results from real-time RT-PCR of total RNA from whole blood samples of cattle using a LIGHTCYCLER instrument and the experimental setting as described in FIG. 4. Solid lines with circles indicate individual RT-PCR experiments with samples from BSE-infected animals, dotted lines indicate BSE-free animals. The Figure further illustrates the crossing point data given in Table 2. The ordinate indicates the values for fluorescence (F2/back-F1) as determined by the LIGHTCYCLER instrument, the abscissa indicates cycle numbers The water control is marked by "$H_2O$".

Figure 9:
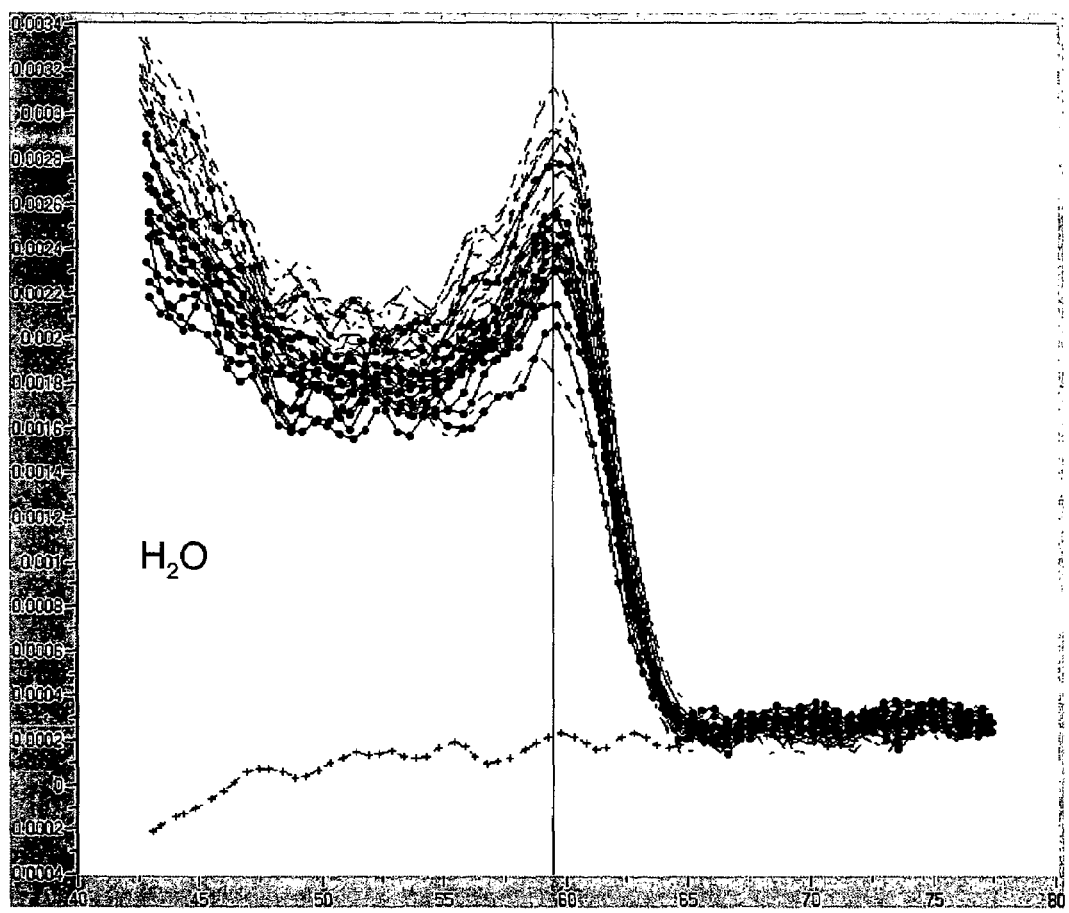

FIG. 9: LT3, melting curves. Results from melting curve analysis of total RNA from whole blood samples of cattle using a LIGHTCYCLER instrument and the experimental setting as described in FIG. 4. Solid lines with circles indicate individual RT-PCR experiments with samples from BSE-infected animals, dotted lines indicate BSE-free animals, solid line indicate control plasmid. As expected the Figure illustrates comparable melting curve shape and melting temperature for all samples. The ordinate indicates the values for fluorescence (F2/back-F1) as determined by the LIGHTCYCLER instrument, the abscissa indicates the reaction temperature. The water control is marked by "$H_2O$".

Figure 10:
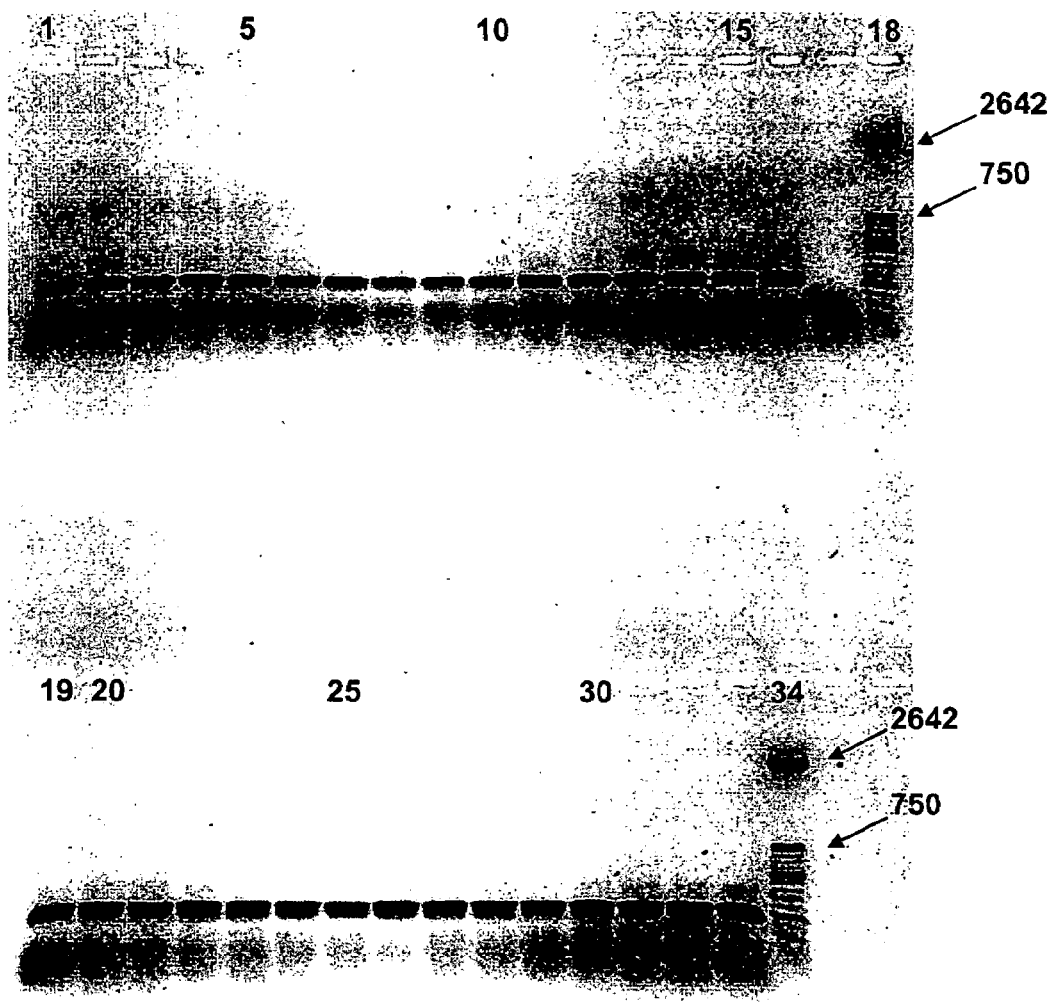

FIG. 10: LT3 Gel. Agarose gel showing RT-PCR product of amplification with LT3 primers from BSE-infected and non-infected control animals. Size marker, fragment sizes in base pairs are indicated on the left. The gel was stained using SYBR Green Gel Stain (Molecular Probes). RT-PCR products compared to marker DNA are of expected size (about 250 bp band; exact size: 244 bp).

By sequencing the LT3 RT-PCR product of biological samples showed a 100% nucleotide sequence identity with control plasmid and splicing marker sequence.

Further description of the samples:

Lane 1 to 10: RT-PCR products from samples of BSE-infected animals in the late stage of the disease (naturally infected, post-mortem positive).

Lane 11 to 15: RT-PCR products from samples of BSE-infected animals in the early stage of the disease (experimentally infected).

Lane 16: LT3 control plasmid (positive control).

Lane 17: water control (negative control).

Lane 18: DNA Molecular Weight Marker XIII (50-750 bp, Roche Diagnostics (catalogue no. 1 721 925). Mixture of restriction fragment sizes are 50, 100, 150, 200, 250, 500, 750 (black arrow), 2642 (black arrow).

Lane 19 to 33: RT-PCR products from samples of BSE-free animals.

Lane 34: DNA Molecular Weight Marker XIII (50-750 bp, Roche Diagnostics (catalogue no. 1 721 925). Mixture of restriction fragment sizes are 50, 100, 150, 200, 250, 500, 750 (black arrow), 2642 (black arrow).

Figure 11:
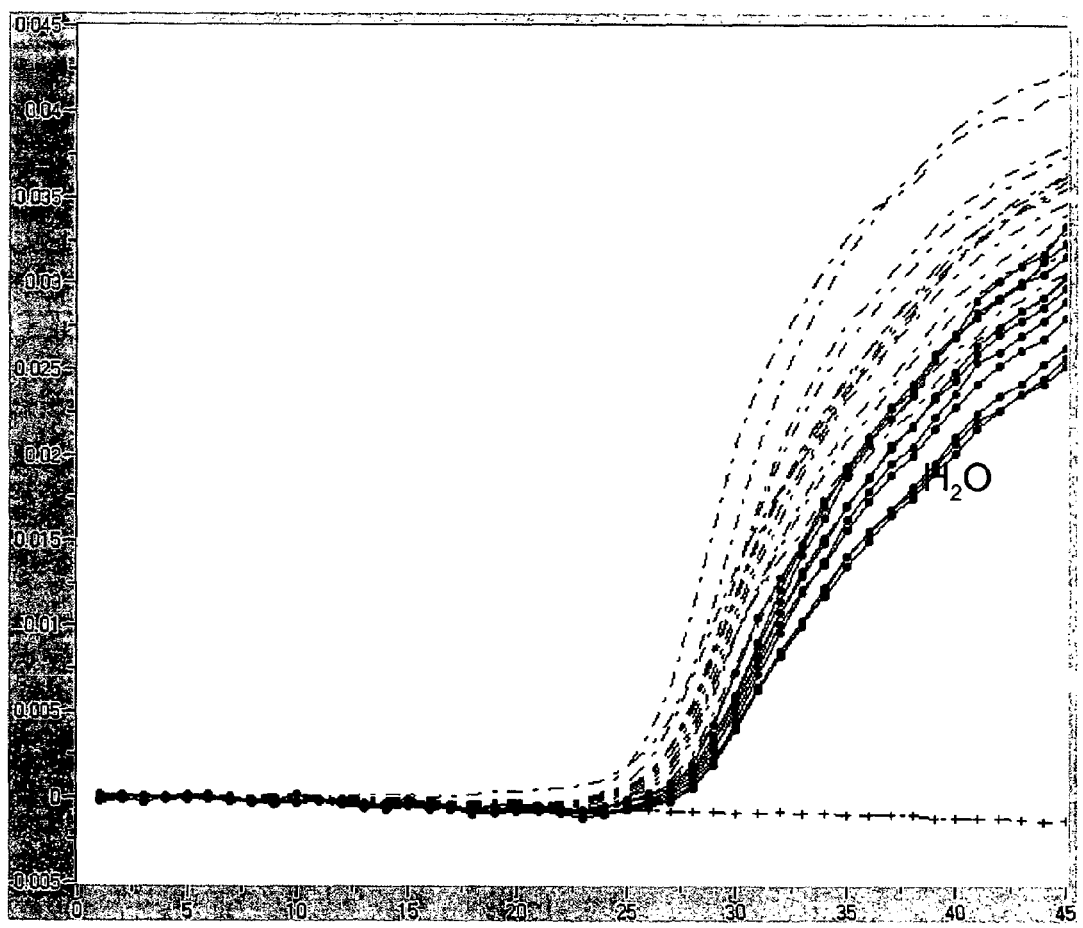

FIG. 11: LT4 amplification curves. Results from real-time RT-PCR of total RNA from whole blood samples of cattle using a LIGHTCYCLER instrument and the experimental setting as described in FIG. 4. Solid lines with circles indicate individual RT-PCR experiments with samples from BSE-infected animals, dotted lines indicate BSE-free animals. The Figure further illustrates the crossing point data given in Table 3. The ordinate indicates the values for fluorescence (F2/back-F1) as determined by the LIGHTCYCLER instrument, the abscissa indicates cycle numbers The water control is marked by "$H_2O$".

Figure 12:
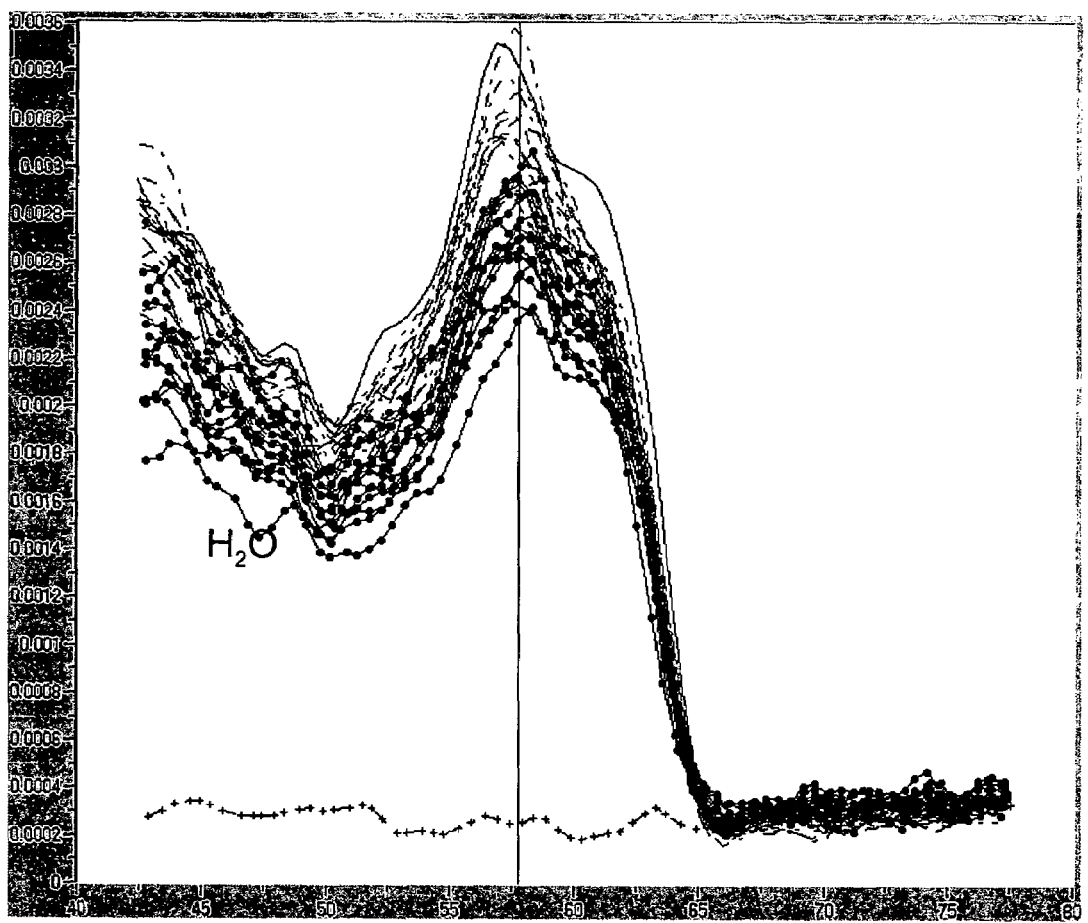

FIG. 12: LT4, melting curve. Results from melting curve analysis of total RNA from whole blood samples of cattle using a LIGHTCYCLER instrument and the experimental setting as described in FIG. 4. Solid lines with circles indicate individual RT-PCR experiments with samples from BSE-infected animals, dotted lines indicate BSE-free animals, solid line indicate control plasmid. As expected the Figure illustrates comparable melting curve shape and melting temperature for all samples. The ordinate indicates the values for fluorescence (F2/back-F1) as determined by the LIGHTCYCLER instrument, the abscissa indicates the reaction temperature. The water control is marked by "$H_2O$ ".

Figure 13:
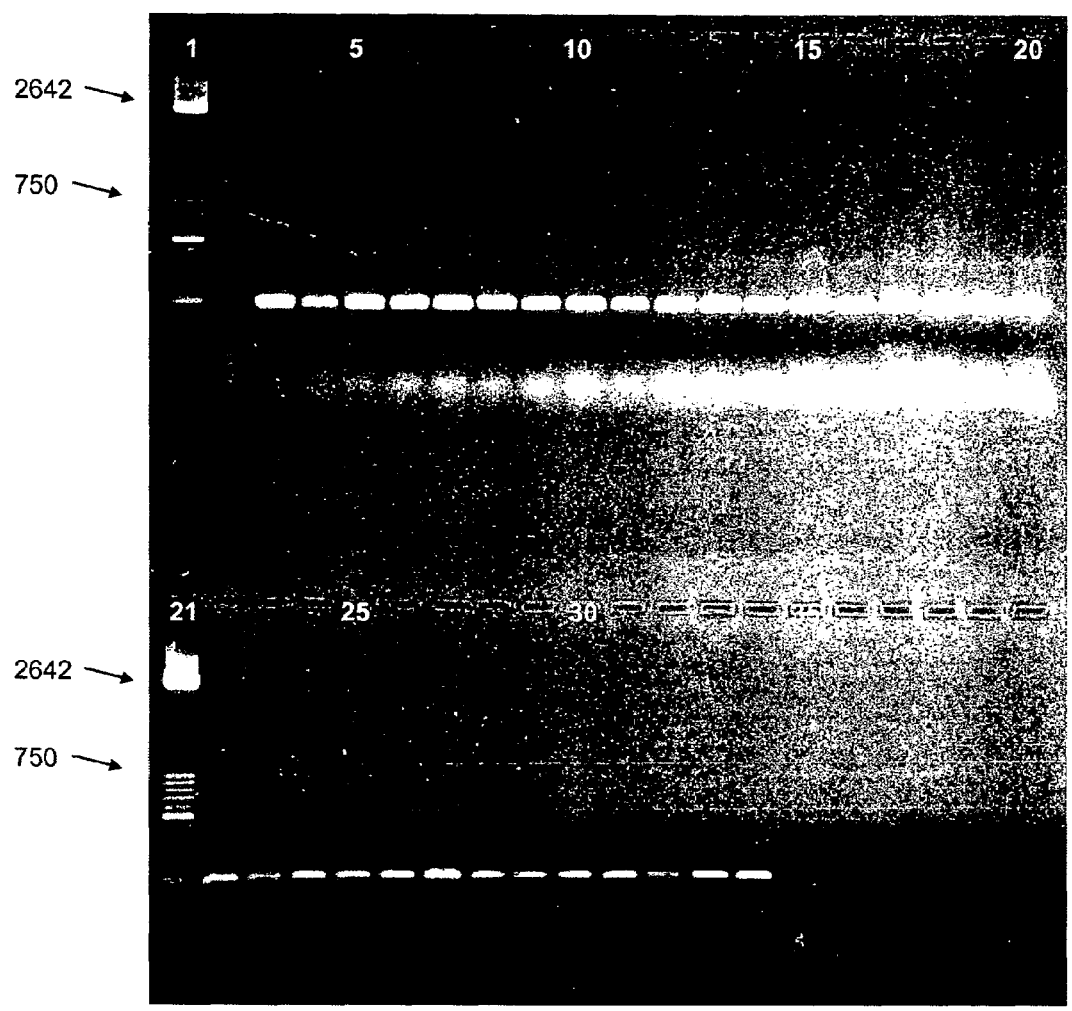

FIG. 13: LT4 Gel. Agarose gel showing RT-PCR product of amplification with LT4 primers from BSE-infected and non-infected control animals. Size marker, fragment sizes in base pairs are indicated on the left. The gel was stained using SYBR Green Gel Stain (Molecular Probes). RT-PCR products compared to marker DNA are of expected size (about 250 bp band; exact size: 253 bp).

By sequencing the LT4 RT-PCR product of biological samples showed a 100% nucleotide sequence identity with control plasmid. Control plasmid showed 1 base-pair exchange when compared to splicing marker sequence.

Further description of the samples:

Lane 1: DNA Molecular Weight Marker XIII (50-750 bp, Roche Diagnostics catalogue no. 1 721 925). Mixture of restriction fragment sizes are 50, 100, 150, 200, 250, 500, 750 (black arrow), 2642 (black arrow).

Lane 2: water control (negative control).

Lane 3 to 17: RT-PCR products from samples of BSE-free animals.

Lane 18 to 20: RT-PCR products from samples of BSE-infected animals in the late stage of the disease (naturally infected, post-mortem positive).

Lane 21: DNA Molecular Weight Marker XIII (50-750 bp, Roche Diagnostics (catalogue no. 1 721 925). Mixture of restriction fragment sizes are 50, 100, 150, 200, 250, 500, 750 (black arrow), 2642 (black arrow).

Lane 22 to 28: RT-PCR products from samples of BSE-infected animals in the late stage of the disease (naturally infected, post-mortem positive).

Lane 29 to 33: RT-PCR products from samples of BSE-infected animals in the early stage of the disease (experimentally infected).

Lane 34: LT4 control plasmid (positive control).

Lane 35: water control (negative control).

DETAILED DESCRIPTION OF THE INVENTION

A sufficient amount of pure and undegraded nucleic acids is the precondition for sensitive detection of a target nucleic acid from a whole blood sample. The inventors surprisingly found rapid stabilization after sampling with chaotrope in combination with shock-freezing thereafter provide the means for isolating nucleic acids of high quality. In addition, the method of the invention allows to store the frozen stabilized sample for at least 2 years. Thus, a first embodiment of the invention is a method for purifying nucleic acids from a whole blood sample, comprising the steps of (a) providing a whole blood sample from a mammal, whereby the sample is not older than 5 minutes; (b) subsequently mixing the sample with anticoagulant; (c) mixing the composition of (b) with an aequous stabilization reagent comprising a non-ionic detergent and a guanidinium salt, whereby the final concentration of the guanidinium salt in the resulting mixture is between 15% and 35% weight by volume, and the final concentration of the non-ionic detergent in the resulting mixture is between 3% and 10% volume by volume; (d) incubating the composition of (c); (e) subsequently shock-freezing the composition, thereby solidifying the composition homogeneously; (f) optionally storing the composition of step (e) in a frozen, solidified state; (g) thawing the frozen composition of step (e) in the presence of an aequous lysis reagent comprising a guanidinium salt, whereby the volume of the lysis buffer adjusts the final concentration of the guanidinium salt in the resulting mixture after thawing to a concentration of between 3.5 M and 4.2 M; (h) adsorbing the nucleic acids contained in the composition of step (g) (liquid phase) to a solid phase, separating the solid phase from the liquid phase, optionally washing the solid phase with the adsorbed nucleic acids and subsequently desorbing the nucleic acids from the solid phase with an elution buffer, thereby purifying said nucleic acids.

Preferably, the anticoagulant of step (b) is an agent capable of forming complexes with divalent cations. Citrate, heparin or EDTA are very much preferred. It is also preferred that the incubation of step (d) is performed at a temperature between 15° C. and 25° C., more preferred at room temperature. It is also advantageous that the incubation of step (d) is performed under constant agitation, for example on a laboratory roller device or a shaker.

Preferably the final concentration of the guanidinium salt in the resulting mixture of step (c) is between 15% and 25% weight by volume, more preferred between 17% and 22% weight by volume, even more preferred 20%. Preferably the final concentration of the non-ionic detergent in the resulting mixture of step (c) is between 5% and 7% volume by volume, even more preferred about 6.5%. A very much preferred non-ionic detergent is Triton X-100.

The incubation step (d) is preferably performed for 5 to 20 minutes, more preferred for about 10 minutes.

It is further preferred that in step (g) prior to thawing dithiothreitol (DTT) is added to the frozen composition of step (e) whereby the concentration of DTT in the resulting mixture after thawing is between 0.01% and 0.1% weight by volume. Very much preferred is a concentration of between 0.03% and 0.07% weight by volume. Even more preferred is 0.06% weight by volume. Also preferred in step (g) the final concentration of the guanidinium salt in the mixture is between 3.5 M and 4.2 M after thawing. Furthermore preferred, the thawing process of step (g) is performed under constant agitation.

The elution buffer of step (h) is a low salt buffer capable of desorbing nucleic acids from the solid phase. The volume of the elution buffer is chosen such that a concentration of nucleic acids in the range of between 1.5 and 15 ng/µl results.

Another embodiment of the invention is a composition comprising whole blood, an anticoagulant, a guanidinium salt, and a non-ionic detergent in a frozen and homogeneously solid state of aggregation.

Yet, another embodiment of the invention is a method of determining the presence of a target nucleic acid in a whole blood sample, comprising the steps of (a) purifying nucleic acids from the whole blood sample according to the method of any of the claims 1 to 5; (b) detecting among the purified nucleic acids of step (a) the presence of the target nucleic acid, thereby determining the presence of the target nucleic acid. In a preferred embodiment of the invention the target nucleic acid is RNA or DNA.

As a consequence of TSE the expression of certain RNAs is changed in several cell types. Detection of such changes can be used for diagnosing TSE, thereby offering an alternative to immunological assays for prion protein, e.g. $PrP^{sc}$. To this end, amplification of nucleic acid sequences by means of the polymerase chain reaction (also referred to as PCR; U.S. Pat. Nos. 4,683,202, 4,683,195, 4,800,159, and 4,965,188) provides a sensitive detection means which is amenable to high-throughput testing.

PCR typically employs two oligonucleotide primers that bind to a selected nucleic acid template (e.g. a DNA or a cDNA). Primers useful in the present invention include oligonucleotides capable of acting as a point of initiation of nucleic acid synthesis within LT1, LT3 or LT4. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

If the target nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min.

If the double-stranded nucleic acid is denatured by heat, the reaction mixture is allowed to cool to a temperature that promotes annealing of each primer to its target sequence on the target nucleic acid. The temperature for annealing is usually from about 35° C. to about 65° C. Annealing times can be from about 10 secs to about 1 min. The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° to 80° C.). Extension times can be from about 10 secs to about 5 mins.

In a very much preferred embodiment of the invention the target nucleic acid is RNA and step (b) of the method of determining the presence of a target nucleic acid in a whole blood sample comprises (i) reverse transcribing the RNA to form a cDNA, (ii) subsequently amplifying, by means of the polymerase chain reaction, the cDNA, (iii) detecting the presence of the cDNA, thereby determining the presence of the target nucleic acid. Also very much preferred, prior to step (i) the RNA concentration is adjusted to a standard value.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Studies using the DATAS approach (WO2005/049863) have identified five bovine nucleic acid sequences as markers for TSE in RNA isolates from whole blood (target nucleotide sequences). Surprisingly it has been found that SEQ ID NOs: 1, 6, and 11 are particularly advantageous since in an experimental setting using the preparation method for nucleic acids according to the invention and real time PCR they are able to discriminate between TSE-infected and non-infected animals.

Therefore, the present invention is used for assessing TSE in cattle. In a further preferred embodiment of the invention a whole blood sample is taken from a living bovine animal. Even more preferred, the whole blood sample is obtained from an animal which is to proceed to the abattoir and to be processed for the human food chain later on. In this regard, the method of the invention can also be performed in combination with an immunological test detecting infectious prion protein ($PrP^{sc}$) or protease-resistant prion protein ($PrP^{res}$).

According to the method of the invention, RNA from whole blood samples is analyzed. In a further preferred embodiment of the invention the whole blood sample is taken from a living bovine animal. Even more preferred, the bovine animal is asymptomatic with respect to TSE. An example therefor is a bovine animal which is to proceed to the abattoir and about to enter the human food chain.

When assessing TSE in a bovine animal the target nucleic acid is preferably selected from the group consisting of SEQ ID NO:1, SEQ ID NO:6, and SEQ ID NO:11 or a subfragment of any of said sequences. Very much preferred, the amplified cDNA is detected using a fluorescent signal. Even more preferred, the amplified cDNA is detected by monitoring the amplification in real time and determining the amount of amplification product after each cycle.

Detection of the amplified target nucleic acid is possible by several means. In a preferred embodiment of the invention, the amplified target nucleic acid is detected using a fluorescent signal. Several detection formats based on target nucleic acid dependent fluorescent signaling have been disclosed, which enable continuous monitoring of the generation of amplification products (reviewed in Wittwer, et al., Biotechniques, 22, (1997) 130-138). These detection formats include but are not limited to (1) to (4):

(1) Use of fluorescent double-stranded DNA recognizing compounds: Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which like SYBR Green I (Molecular Probes), for example, do not affect the efficiency of the PCR reaction. In a very much preferred embodiment of the invention, the target nucleic acid is detected by monitoring the amplification in real time and determining the amount of amplification product after each cycle. The fluorescent signal generated by the incorporated dye can be quantified. Signal strength correlates with the amount of PCR product formed and thus allows quantification of the target nucleic acid after each circle. Therefore, in an even more preferred embodiment of the invention the target nucleic acid is detected by monitoring the amplification in real time and determining the amount of amplification product after each cycle.

(2) Increased fluorescence resonance energy transfer (FRET) upon hybridization: For this detection format, two oligonucleotide hybridization probes each labeled with a fluorescent moiety are used which are capable of hybridizing to adjacent but non overlapping regions of one strand of the amplification product. Preferably, one oligonucleotide is labeled at the 5' end and the second oligonucleotide is labeled at the 3' end. When hybridized to the target DNA, the two fluorescent labels are brought into close contact, such that fluorescence resonance energy transfer between the two fluorescent moieties can take place. As a consequence, the hybridization can be monitored through excitation of the donor moiety and subsequent measurement of fluorescence emission of the second acceptor moiety. In a similar embodiment, only one fluorescently labeled probe is used, which together with one appropriately labeled primer may also serve as a specific FRET pair (Bernard, P.S., et al., Anal. Biochem. 255 (1998) 101-107). In a very much preferred embodiment of the invention, the target nucleic acid is detected with FRET hybridization probes. Independent from the detection format or fluorescent label, hybridization probes are always polynucleotides having sequences which are completely identical with or exactly complementary to the sequence of the target nucleic acid. Yet, it is also within the scope of the invention if the probes contain one or several mismatches, as long as they are capable of hybridizing to the amplification product under appropriate hybridization conditions. In any case, it has been proven to be particular advantageous, if the sequence identity or complementarity is 100% over a range of at least 10 contiguous residues. Taking onto account the length of the amplified fragments in the method of the invention, the length of the probe does not exceed 40 nucleotides, preferably not more than 30 nucleotides. However, hybridization probes may have 5' or 3' overhangs which do not hybridize to the target nucleic acid.

(3) Hydrolysis probes used in TAQMAN instruments: In order to detect the amplification product, a single-stranded hybridization probe is used, which is labeled with a fluorescent entity, the fluorescence emission of which is quenched by a second label on the same probe which may act as a quenching compound. During the annealing step of the PCR reaction, the probe hybridizes to its target sequence, and, subsequently, during the extension of the primer, the DNA polymerase having a 5'-3'-exonuclease activity hydrolyzes the hybridization probe, such that the fluorescent entity is separated from the quencher compound. After appropriate excitation, fluorescence emission can be monitored as an indicator of accumulating amplification product.

(4) Molecular beacons: Similar to hydrolysis probes, a molecular beacon oligonucleotide is labeled with a fluorescent compound and a quencher compound, which due to the secondary structure of the molecule are in dose vicinity to each other. Upon binding to the target DNA, the intramolecular hydrogen bonding is broken, and the fluorescent compound located at one end of the probe is separated from the quencher compound, which is located at the opposite end of the probe (U.S. Pat. No. 5,118,801).

A very much preferred embodiment of the invention is a method of assessing TSE in a bovine animal by way of determining the presence of a target nucleic acid in a preparation of nucleic acids from whole blood sample comprising the steps of performing at least one cycling step, wherein a cycling step comprises an amplifying step and hybridizing step, wherein said amplifying step comprises contacting said sample with a pair of LT1, LT3 or LT4 primers to produce LT1, LT3 or LT4 amplification product if a target nucleic acid LT1 (SEQ ID NO:1), LT3 (SEQ ID NO:6), or LT4 (SEQ ID NO:11) is present in said sample, wherein said hybridizing step comprises contacting said sample with a pair of LT1, LT3 or LT4 probes, wherein the members of said pair of LT1, LT3 or LT4 probes hybridize within no more than five nucleotides of each other, wherein a first LT1, LT3 or LT4 probe of said pair of LT1, LT3 or LT4 probes is labelled with a donor fluorescent moiety and said second LT1, LT3 or LT4 probe of said pair of LT1, LT3 or LT4 probes is labelled with a corresponding acceptor fluorescent moiety; and detecting the presence or absence of fluorescence resonance energy transfer (FRET) between said donor fluorescent moiety of said first LT1, LT3 or LT4 probe and said acceptor fluorescent moiety of said second LT1, LT3 or LT4 probe, wherein the presence of FRET is indicative of the presence of transmissible spongiform encephalopathy (TSE) in the individual from which said sample, derives and wherein the absence of FRET in indicative of the absence of TSE in said individual.

Preferably, the LT1 primer pair consists of the oligonucleotides according to SEQ ID NO:2. and SEQ ID NO:3; the LT3 primer pair consists of the oligonucleotides according to SEQ ID NO:7 and SEQ ID NO:8; and LT4 primer pair consists of the oligonucleotides according to SEQ ID NO:12. and SEQ ID NO:13.

Also preferred, the pair of LT1 probes consists of the oligonucleotides according to SEQ ID NO:4 and SEQ ID NO:5; the pair of LT3 probes consists of the oligonucleotides according to SEQ ID NO:9 and SEQ ID NO:10; and the pair of LT4 probes consists of the oligonucleotides according to SEQ ID NO:14 and SEQ ID NO:15.

The oligonucleotide primers are combined with PCR reagents under reaction conditions that induce primer extension. For example, chain extension reactions typically include 3.25 mM Manganese acetate, 0.5 µM forward primer, 0.5 µM reverse primer, 0.2 µM fluorescein probe, and 0.2 µM LCRed640 probe. The reactions usually contain 150 to 320 µM each of dATP, dCTP, dTTP, dGTP, or one or more analogs thereof.

The amplification products generated during this process can be visualized using gel electrophoresis or by way of hybridization using specific probes. In addition, methods are known to the art which allow to monitor the amplification of a target nucleic acid in real time (WO 97/46707, WO 97/4671., WO 97/46714).

Most preferred in this regard is monitoring the amplification by way of detecting fluorescence resonance energy transfer (FRET). FRET technology (see, for example, U.S. Pat. Nos. 4,996,143, 5,565,322, 5,849,489, and 6,162,603) is based on a concept that when a donor and a corresponding acceptor fluorescent moiety are positioned within a certain distance of each other, energy transfer takes place between the two fluorescent moieties that can be visualized or otherwise detected and/or quantitated. Two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product nucleic acid at the appropriate positions, a FRET signal is generated. Hybridization temperatures can range from about 35 to about 65° C. for about 10 secs to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 44. nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-Acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-Acetamido-4'-isothiocyanatostilbene-2,2'-disulfonic acid derivatives. Representative acceptor fluorescent moieties, depending upon the donor fluorescent moiety used, include LC™-Red 640, LC™-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, USA) or Sigma Chemical Co. (St. Louis, USA).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LC™-Red 640-NHS-ester can be combined with C6-Phosphoramidites (available from ABI (Foster City, USA) or Glen Research (Sterling, USA)) to produce, for example, LC™-Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, USA)), or 3'-amino-CPG's that require coupling of a fluorescein-NHS-ester after oligonucleotide synthesis.

Before detection of the target nucleic acid, the fraction encompassing all nucleic acids (DNA and RNA) is purified from the sample which is a complex mixture of different components. Often, for the first steps, processes are used which allow the enrichment of the nucleic acids. To release the contents of cells, they may be treated with enzymes or with chemicals to dissolve, degrade or denature the cellular walls. This process is commonly referred to as lysis. The resulting solution containing such lysed material is referred to as lysate. A problem often encountered during the lysis is that other enzymes degrading the component of interest, e.g. ribonucleases degrading RNA, come into contact with the component of interest during lysis. These degrading enzymes may also be present outside the cells or may have been spatially separated in different cellular compartments before the lysis and come now into contact with the component of interest. It is common to use chaotropic agents as e.g. guanidinium thiocyanate or anionic, cationic, zwitterionic or non-ionic detergents when nucleic acids are intended to be set free. It is also an advantage to use proteases which rapidly degrade these enzymes or unwanted proteins. However, this may produce another problem as the said substances or enzymes can interfere with reagents or components in subsequent steps. Proteases (see Walsh, Enzymatic Reaction Mechanisms. W. H. Freeman and Company, San Francisco, Chapter 3 (1979) which are commonly known to the are e.g. alkaline proteases (WO 98/04730) or acid proteases (U.S. Pat. No. 5,386,024). The protease which is widely used in the prior art for sample preparation for the isolation of nucleic acids is proteinase K from *Tritirachium album l* (see e.g. Sambrook, J. et al., *Molecular Cloning: A Laboratory Manual*, Cold Spring Harbor Laboratory Press, Cold Spring Harbor, N.Y., 1989) which is active around neutral pH and belongs to a family of proteases known as subtilisins.

In the next steps of the sample preparation which follow on the lysis step, the nucleic acids are further enriched. There are several methods for the extraction of nucleic acids: (A) sequence-dependent or biospecific methods such as e.g.: affinity chromatography and hybridisation to immobilised probes; (B) sequence-independent or physico-chemical methods such as e.g.: liquid-liquid extraction (e.g. with phenol-chloroform), precipitation (e.g. with pure ethanol), extraction with filter paper, extraction with micelle-forming agents (e.g. cetyl-trimethyl-ammonium-bromide), binding to immobilised intercalating dyes (e.g. acridine derivatives), adsorption to silica gel or diatomic earths, and adsorption to magnetic glass particles (MGP) or organo silane particles under chaotropic conditions. Particularly interesting for extraction purposes is the adsorption of nucleic acids to a glass surface although other surfaces are possible. Many procedures for isolating nucleic acids from their natural environment have been proposed in recent years by the use of their binding behavior to glass surfaces. If unmodified nucleic acids are the target, a direct binding of the nucleic acids to a material with a silica surface or glass is preferred because among other reasons the nucleic acids do not have to be modified and even native nucleic acids can be bound. To separate the particles from the contaminants, the particles may be either centrifuged or fluids are drawn through glass fiber filters. This is a limiting step, however, that prevents the procedure from being used to process large quantities of samples. The use of magnetic particles to immobilize nucleic acids after precipitation by adding salt and ethanol is more advantageous and described e.g. in Alderton, R. P., et al., Anal. Biochem. 201 (1992) 166-169 and WO 91/12079. In this procedure, the nucleic acids are agglutinated along with the magnetic particles. The agglutinate is separated from the original solvent by applying a magnetic field and performing a washing step. After one or more washing steps, the nucleic acids are dissolved in a Tris buffer. Magnetizable particular adsorbents proved to be very efficient and suitable for automatic sample preparation. Ferrimagnetic and ferromagnetic as well as superparamagnetic pigments are used for this purpose. The most preferred magnetic glass particles and methods using these are described in WO 01/37291.

After the purification or isolation of the nucleic acids including the target nucleic acid from their natural surroundings, the target nucleic acid may be detected. Before detection, however, in an additional step the nucleic acids are incubated with RNase-free DNase, thereby allowing to specifically purify the RNAs which were present in the sample. Example 2 describes a preferred method of sample preparation using the MAGNA PURE LC instrument and an RNA isolation kit (Roche Diagnostics GmbH, Mannheim, Germany).

The target nucleic acid is detected by way of specific amplification using RT-PCR (RT=reverse transcriptase; PCR=polymerase chain reaction). The target RNA is first reverse-transcribed to form a complementary single-stranded cDNA. The cDNA in turn serves as a template for DNA amplification using suitable primers. The amplification product is also referred to as the "target nucleic acid".

In the method of the invention, a preferred target sequence selected from the group consisting of SEQ ID NOs: 1, 6, and 11 or a partial sequence thereof or a combination of the sequences of SEQ ID NOs: 1, 6, and 11 or partial sequences thereof or all three sequences or partial sequences thereof are amplified by means of PCR using specific primer pairs. A primer pair consisting of one forward primer and one reverse primer is used in the method of the invention. In the amplification reaction mixture the preferred initial concentration of each primer is 0.5° µM.

The forward primer is an oligonucleotide with a preferred length of between 15 and 25 nucleotides. Preferably, the sequence of the primer is a contiguous partial sequence of the respective preferred target nucleotide sequence selected from the group consisting of SEQ ID NOs: 1, 6, and 11. The reverse primer is an oligonucleotide with a preferred length of between 15 and 25 nucleotides. Also preferred, the sequence of the primer is a contiguous partial sequence of the complement of the respective preferred target nucleotide sequence selected from the group consisting of SEQ ID NOs: 1, 6, and 11. Although there are numerous possibilities to design such primers, there are preferred primer sequences according to the invention.

Preferably, the LT1 primer pair consists of the oligonucleotides according to SEQ ID NO:2. and SEQ ID NO:3; the LT3 primer pair consists of the oligonucleotides according to SEQ ID NO:7 and SEQ ID NO:8; and LT4 primer pair consists of the oligonucleotides according to SEQ ID NO:12. and SEQ ID NO:13.

It is noted that the terms "oligonucleotide" and also "polynucleotide" in the context of the present invention summarizes not only (desoxy)-oligo-ribonucleotides, but also all DNA- or RNA-derivatives known in the art like e.g. methyl-phosphonates, phosphothioates, 2'-O-alkyl-derivatives as well as peptide nucleic acids, and analoga comprising modified bases like 7-Deaza-Purines. It is also noted that a primer oligo- or polynucleotide is understood as being capable of serving as a substrate for template-dependent DNA- or RNA-polymerases. By virtue of polymerase activity a primer can be elongated by the addition of nucleoside phosphates or analogues thereof.

The present invention provides methods for detecting the presence or absence of TSE-specific differentially spliced transcripts in a whole blood sample from a bovine individual. Methods provided by the invention avoid problems of sample contamination, false negatives, and false positives. The methods include performing at least one cycling step that includes amplifying a target nucleic acid portion of a LT1, LT3, and/or LT4 nucleic acid molecule from a sample using a pair of LT1, LT3, and/or LT4 primers, respectively. Each of the LT1, LT3, or LT4 primers anneals to a target within or adjacent to a LT1, LT3, or LT4 nucleic acid molecule, respectively, such that at least a portion of each amplification product contains nucleic acid sequence corresponding to LT1, LT3, or LT4, respectively. More importantly, the amplification product should contain the nucleic acid sequences that are complementary to the LT1, LT3, or LT4 probes, respectively. The LT1, LT3, and/or LT4 amplification product is produced provided that target nucleic acid (TSE-specific and differentially spliced mRNA) is present. Each cycling step further includes contacting the sample with a pair of LT1, LT3, and/or LT4 probes. According to the invention, one member of each pair of the LT1, LT3, and/or LT4 probes is labeled with a donor fluorescent moiety and the other is labeled with a corresponding acceptor fluorescent moiety. The presence or absence of FRET between the donor fluorescent moiety of the first LT1, LT3, or LT4 probe and the corresponding acceptor fluorescent moiety of the second LT1, LT3, or LT4 probe, respectively, is detected upon hybridization of the LT1, LT3, or LT4 probes to the respective amplification product.

Each cycling step includes an amplification step and a hybridization step, and each cycling step is usually followed by a FRET detecting step. Multiple cycling steps are performed, preferably in a thermocycler. Methods of the invention can be performed using one or more of the LT1, LT3, and/or LT4 primer and probe sets to detect the presence of the respective target nucleic acid(s). Alternatively, methods of the invention can be performed simultaneously with each of the LT1, LT3, and LT4 primer and probe sets to detect the respective target sequences in whole blood samples.

As used herein, "amplifying" refers to the process of synthesizing nucleic acid molecules that are complementary to one or both strands of a template nucleic acid molecule (e.g., LT1, LT3, or LT4 nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum Taq) and an appropriate buffer and/or co-factors for optimal activity of the polymerase enzyme (e.g., $MgCl_2$ and/or KCl).

If amplification of a target nucleic acid occurs and an amplification product is produced, the step of hybridizing results in a detectable signal based upon FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

Generally, the presence of FRET indicates TSE infection of the bovine individual from which the respective blood sample was taken; the absence of FRET indicates the absence of TSE. Inadequate specimen collection, transportation delays, inappropriate transportation conditions, among other factors can affect the success and/or accuracy of a test result, however. Using the methods disclosed herein, detection of FRET within 45 cycling steps is indicative of TSE infection.

In a most preferred embodiment of the invention, the amplification product is detected with FRET hybridization probes. Independent from the detection format or fluorescent label, hybridization probes are always polynucleotides having sequences which are completely identical with or exactly complementary to the sequence of the target nucleic acid. Yet, it is also within the scope of the invention if the probes contain one or several mismatches, as long as they are capable of hybridizing to the amplification product under appropriate hybridization conditions. In any case, it has been proven to be particular advantageous, if the sequence identity or complementarity is 100% over a range of at least 10 contiguous residues. Taking onto account the length of the amplified fragments in the method of the invention, the length of a probe does not exceed 40 nucleotides, preferably not more than 30 nucleotides. However, hybridization probes may have 5' or 3' overhangs which do not hybridize to the target nucleic acid.

Preferably, the pair of LT1 probes consists of the oligonucleotides according to SEQ ID NO:4 and SEQ ID NO:5; the pair of LT3 probes consists of the oligonucleotides according to SEQ ID NO:9 and SEQ ID NO:10; and the pair of LT4 probes consists of the oligonucleotides according to SEQ ID NO:14 and SEQ ID NO:15.

According to the invention, it is furthermore preferred that a first and the second target sequence are amplified and detected in one tube. This is possible in a multiplex approach, wherein differentially labeled hybridization probes for each sequence are used for detection of the respective amplification products.

The assays of the invention may be performed on a LIGHT-CYCLER instrument (Roche Diagnostics GmbH, Mannheim, Germany) using a pair of FRET hybridization probes labeled with Fluorescein at the 3' end of the first hybridization probe and with LC-Red-640 (Roche Diagnostics GmbH, Mannheim, Germany) at the 5' end of the second hybridization probe. When performing multiplex analysis with two different target sequences, a second pair of FRET hybridization probes labeled with Fluorescein at the 3' end of the first oligonucleotide and with LC-Red-705 (Roche Diagnostics GmbH, Mannheim, Germany) at the 5' end of the second oligonucleotide are preferably used.

Principally, any kind of quantification method can be applied, however, it has been proven to be advantageous, if methods using an external standard are applied. The external standard itself may be a plasmid or a linearized template with one or more target sequences to be amplified.

In case of quantification of a nucleic acid using external standards, a calibration curve has to be generated. For this calibration curve, known amounts of the target nucleic acid are amplified and the intensity of fluorescent signal is determined as a function of cycle number. After smoothening of the kinetics by a mathematical fit, the first or second maximum of the derivative are calculated. This enables a correlation between the original target concentration and the fractional cycle number of a determined maximum. Subsequently, determination of unknown analyte concentrations may be performed.

In order to eliminate quantification errors originating from different detection sensitivities, it has been proven to be particular advantageous, if the same batch of hybridization probe(s) is used for the sample to be analyzed and for the calibration samples.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the LT1, LT3, or LT4 probes from the respective amplification product can confirm the presence or absence of the respective target nucleic acid in the sample.

Within each thermocycler run, control samples are cycled as well. Positive control samples can amplify a control template (other than LT1, LT3, or LT4) using, for example, control primers and control probes. Positive control samples can also amplify, for example, a plasmid construct containing LT1, LT3, or LT4 nucleic acid molecule. Such a plasmid control can be amplified internally (e.g., within the sample) or in a separate sample run side-by-side with the individuals' samples. Each thermocycler run should also include a negative control that, for example, lacks target template DNA.

Such controls are indicators of the success or failure of the amplification, hybridization and/or FRET reaction. Therefore, control reactions can readily determine, for example, the ability of primers to anneal with sequence-specificity and to initiate elongation, as well as the ability of probes to hybridize with sequence-specificity and for FRET to occur.

Conventional PCR methods in conjunction with FRET technology can be used to practice the methods of the invention. In one embodiment, a LIGHTCYCLER instrument is used. A detailed description of the LIGHTCYCLER System and real-time and on-line monitoring of PCR can be found at http://biochem.roche.com/lightcycler. The following patent applications describe real-time PCR as used in the LIGHTCYCLER technology: WO 97/46707, WO 97/46714 and WO 97/46712. The LIGHTCYCLER instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LIGHTCYCLER thermal chamber. Addition of selected fluorescent dyes to the reaction components allows the PCR to be monitored in real time and on-line. Furthermore, the cuvettes serve as an optical element for signal collection (similar to glass fiber optics), concentrating the signal at the tip of the cuvette. The effect is efficient illumination and fluorescent monitoring of microvolume samples.

The LIGHTCYCLER carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorometer, as part of the LIGHTCYCLER apparatus, houses the light source. The emitted light is filtered and focused by an epi-illumination lens onto the top of the cuvette. Fluorescent light emitted from the sample is then focused by the same lens, passed through a dichroic mirror, filtered appropriately, and focused onto data-collecting photohybrids. The optical unit available in the LIGHTCYCLER 1.2 instrument (Roche Applied Science, Catalog No. 2011468) includes three bandpass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LIGHTCYCLER can be operated using a PC workstation and can utilize a Windows operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

The following examples, sequence listing and figures are provided to aid the understanding of the present invention, the true scope of which is set forth in the appended claims. It is understood that modifications can be made in the procedures set forth without departing from the spirit of the invention.

SPECIFIC EMBODIMENTS

EXAMPLE 1

Blood Samples (Cattle)

A first set of whole blood samples came from 10 animals which were shown to be infected with BSE by means of a post mortem test which immunologically detects $PrP^{res}$.

A second set of whole blood samples came from 14 healthy animals. They were tested negative using commercially available post-mortem tests.

EXAMPLE 2

Sample Preparation

Figure 1:
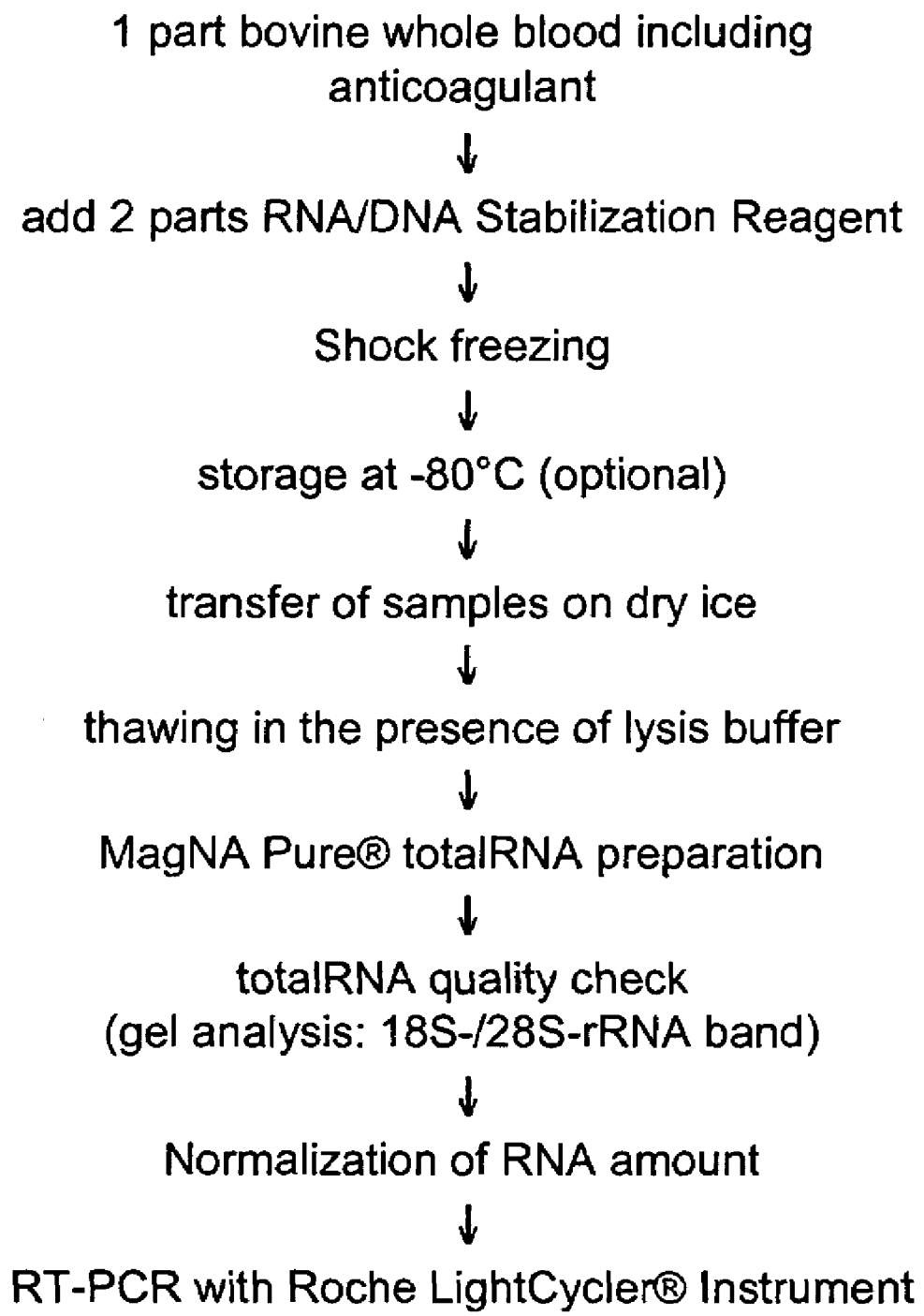
FIG. 1: (1) Sampling/Lysis process: Bovine whole blood samples are anticoagulated with EDTA, 1 part of anticoagulated whole blood is mixed vigorously with 2 parts of RNA/DNA Stabilization Reagent for Blood/Bone Marrow (Roche Diagnostics catalogue no. 1 934 317, pre-heated to 37° C.). Lysis of samples for 10 min at room temperature. Freezing of lysates in liquid nitrogen. Long time storage of samples at −80° C.

Workflow, RNA preparation, also see legend to FIG. 1. Blood was drawn from test animals and immediately mixed with anticoagulant. A typical blood sample had a volume of 50 ml. Using a volume ratio of 2:1 stabilization reagent was added to the blood samples (to result in a final volume of 150 ml) which were subsequently snap-frozen in liquid nitrogen. Frozen samples were transferred to the laboratory on dry ice and stored at −80° C. if necessary. Before thawing the stabilized samples 150 mg solid DTT were added onto the solid frozen block, followed by 100 ml lysis reagent. Thawing was accomplished at room temperature under constant agitation (laboratory roller). The final concentration of guanidinium salt in the lysed sample was 3.9 M. Aliquots of 900 µl of the lysed sample were subjected to RNA preparation using the MAGNA PURE LC instrument and commercial RNA isolation kits (e.g. Catalogue no. 03542394001) according to the instructions of the supplier (Roche Diagnostics GmbH, Mannheim, Germany).

EXAMPLE 3

Sample Analysis

For setting up the RT-PCR 5 µl of RNA eluate was used in a total reaction volume of 20 µl. A typical RT-PCR consists of 3.25 mM $Mn(OAc)_2$, 0.5 µM of each primer (forward, reverse primer) and 0.2 µM of each LIGHTCYCLER HYBPROBE (fluorescein, LCRed640 HYBPROBE). The PCR specific components were added according to package insert of LightCycler RNA Master Hybridization Probes (Roche Diagnostics catalogue no. 03 018 954 001). After PCR amplification melting curve analysis was performed. For analysis of PCR product size agarose (1.5%) gel electrophoresis was performed.

EXAMPLE 4

Analysis Results

PCR was performed on a LIGHTCYCLER instrument using the protocol as given in FIG. 4. Results are depicted in FIG. 5 (LT1), FIG. 8 (LT3), and FIG. 11 (LT4).

In a PCR amplification reaction, the cycle at which the fluorescence, i.e. in the present case the FRET fluorescence of the detection probes hybridized to the amplified DNA, rises above the background fluorescence is called the "crossing point" of the sample. The crossing point of a sample appears as a sharp upward curve on the experiment's fluorescence chart. The crossing point is the point at which the concentration of the target nucleic acid in the sample.

Table 1 summarizes the crossing point data for LT1.

TABLE 1

| Sample | Status | Crossing point |
|---|---|---|
| H₂O | negative run control | No CP |
| 1 | infected, confirmed by post-mortem test | 30.01 |
| 2 | infected, confirmed by post-mortem test | 29.75 |
| 3 | infected, confirmed by post-mortem test | 30.08 |
| 4 | infected, confirmed by post-mortem test | 30.23 |
| 5 | infected, confirmed by post-mortem test | 29.63 |
| 6 | infected, confirmed by post-mortem test | 30.24 |
| 7 | infected, confirmed by post-mortem test | 30.02 |
| 8 | infected, confirmed by post-mortem test | 29.77 |
| 9 | infected, confirmed by post-mortem test | 30.57 |
| 10 | infected, confirmed by post-mortem test | 29.97 |
|  | BSE, average | 30.03 |
| 11 | healthy, not infected, negative post-mortem test | 29.86 |
| 12 | healthy, not infected, negative post-mortem test | 28.37 |
| 13 | healthy, not infected, negative post-mortem test | 28.57 |
| 14 | healthy, not infected, negative post-mortem test | 28.89 |
| 15 | healthy, not infected, negative post-mortem test | 28.32 |
| 16 | healthy, not infected, negative post-mortem test | 28.51 |
| 17 | healthy, not infected, negative post-mortem test | 28.09 |
| 18 | healthy, not infected, negative post-mortem test | 28.27 |
| 19 | healthy, not infected, negative post-mortem test | 28.46 |
| 20 | healthy, not infected, negative post-mortem test | 28.07 |
|  | healthy, average | 28.54 |

Table 2 summarizes the crossing point data for LT3.

TABLE 2

| Sample | Status | Crossing point |
|---|---|---|
| H₂O | negative run control | No CP |
| 1 | infected, confirmed by post-mortem test | 24.57 |
| 2 | infected, confirmed by post-mortem test | 24.25 |
| 3 | infected, confirmed by post-mortem test | 24.89 |
| 4 | infected, confirmed by post-mortem test | 25.07 |
| 5 | infected, confirmed by post-mortem test | 24.69 |
| 6 | infected, confirmed by post-mortem test | 24.74 |
| 7 | infected, confirmed by post-mortem test | 24.68 |
| 8 | infected, confirmed by post-mortem test | 24.54 |
| 9 | infected, confirmed by post-mortem test | 25.51 |
| 10 | infected, confirmed by post-mortem test | 24.88 |

TABLE 2-continued

| Sample | Status | Crossing point |
|---|---|---|
|  | BSE, average | 24.78 |
| 11 | healthy, not infected, negative post-mortem test | 24.12 |
| 12 | healthy, not infected, negative post-mortem test | 23.91 |
| 13 | healthy, not infected, negative post-mortem test | 23.25 |
| 14 | healthy, not infected, negative post-mortem test | 23.89 |
| 15 | healthy, not infected, negative post-mortem test | 23.71 |
| 16 | healthy, not infected, negative post-mortem test | 24.08 |
| 17 | healthy, not infected, negative post-mortem test | 23.96 |
| 18 | healthy, not infected, negative post-mortem test | 23.24 |
| 19 | healthy, not infected, negative post-mortem test | 23.76 |
| 20 | healthy, not infected, negative post-mortem test | 23.33 |
|  | healthy, average | 23.73 |

Table 3 summarizes the crossing point data for LT4.

TABLE 3

| Sample | Status | Crossing point |
|---|---|---|
| H₂O | negative run control | No CP |
| 1 | infected, confirmed by post-mortem test | 27.19 |
| 2 | infected, confirmed by post-mortem test | 27.84 |
| 3 | infected, confirmed by post-mortem test | 27.71 |
| 4 | infected, confirmed by post-mortem test | 27.96 |
| 5 | infected, confirmed by post-mortem test | 27.76 |
| 6 | infected, confirmed by post-mortem test | 27.53 |
| 7 | infected, confirmed by post-mortem test | 27.91 |
| 8 | infected, confirmed by post-mortem test | 27.58 |
| 9 | infected, confirmed by post-mortem test | 27.80 |
| 10 | infected, confirmed by post-mortem test | 27.65 |
|  | BSE, average | 27.69 |
| 11 | healthy, not infected, negative post-mortem test | 26.57 |
| 12 | healthy, not infected, negative post-mortem test | 26.64 |
| 13 | healthy, not infected, negative post-mortem test | 26.51 |
| 14 | healthy, not infected, negative post-mortem test | 26.49 |
| 15 | healthy, not infected, negative post-mortem test | 26.77 |
| 16 | healthy, not infected, negative post-mortem test | 26.85 |
| 17 | healthy, not infected, negative post-mortem test | 26.60 |
| 18 | healthy, not infected, negative post-mortem test | 26.66 |
| 19 | healthy, not infected, negative post-mortem test | 26.86 |
| 20 | healthy, not infected, negative post-mortem test | 27.17 |
| 21 | healthy, not infected, negative post-mortem test | 26.10 |
| 22 | healthy, not infected, negative post-mortem test | 26.87 |
| 23 | healthy, not infected, negative post-mortem test | 25.51 |
| 24 | healthy, not infected, negative post-mortem test | 25.45 |
|  | healthy, average | 26.5 |

What is claimed is:

1. A method for purifying nucleic acids from a whole blood sample comprising the steps of:
   (a) providing a whole blood sample from a mammal, wherein the sample is not older than 5 minutes;
   (b) mixing the sample with an anticoagulant;
   (c) mixing the sample and anticoagulant with an aqueous stabilization reagent to form a composition, the stabilization reagent comprising a non-ionic detergent and a guanidinium salt, wherein the final concentration of the guanidinium salt in the composition is between 15% and 35% weight by volume, and the final concentration of the non-ionic detergent in the composition is between 3% and 10% volume by volume;
   (d) incubating the composition for about 10 minutes;
   (e) shock-freezing the composition, thereby solidifying the composition homogeneously;
   (f) thawing the frozen composition in the presence of an aqueous lysis reagent comprising a guanidinium salt, wherein the volume of the lysis reagent adjusts the concentration of the guanidinium salt in the thawed composition to between 3.5 M and 4.2 M in the thawed composition, further in the presence of dithiothreitol (DTT), wherein the concentration of DTT in the composition after thawing is between 0.01% and 0.1% weight by volume;
   (g) adsorbing the nucleic acids in the composition from step (f) onto a solid phase; and
   (h) desorbing the nucleic acids from the solid phase with an elution buffer, thereby purifying the nucleic acids.

2. The method of claim 1, wherein the anticoagulant is an agent capable of forming complexes with divalent cations.

3. The method of claim 1, wherein the incubation step is performed at room temperature and under constant agitation.

4. The method of claim 1, wherein the thawing step is performed under constant agitation.

5. A method of determining the presence of a target nucleic acid in a whole blood sample, comprising the steps of:
   purifying nucleic acids from the whole blood sample according to the method of claim 1; and
   detecting the presence of the target nucleic acid in the purified nucleic acids.

6. The method of claim 5, wherein the target nucleic acid is ribonucleic acid or deoxyribonucleic acid.

7. The method of claim 5, wherein the target nucleic acid is ribonucleic acid (RNA) and the detection step comprises (i) reverse transcribing the RNA to form a cDNA, (ii) amplifying, by means of a polymerase chain reaction, the cDNA, and (iii) detecting the presence of the cDNA, thereby determining the presence of the target nucleic acid.

8. The method of claim 7, further comprising adjusting the RNA concentration to a standard value prior to the reverse transcription step.

9. The method of claim 7, wherein the target nucleic acid is selected from the group consisting of SEQ ID NO:1, SEQ ID NO:6, and SEQ ID NO:11.

10. The method of claim 7, wherein the amplified cDNA is detected using a fluorescent signal.

11. The method of claim 7, wherein the amplified cDNA is detected by monitoring the amplification in real time and determining the amount of amplification product after each cycle.

12. The method of claim 11 comprising the steps of:

performing at least one cycling step, wherein a cycling step comprises an amplifying step and hybridizing step, wherein said amplifying step comprises contacting said sample with a pair of LT1, LT3 or LT4 primers to produce LT1, LT3 or LT4 amplification product if a target nucleic acid LT1 (SEQ ID NO:1), LT3 (SEQ ID NO:6), or LT4 (SEQ ID NO:11) is present in said sample, wherein said hybridizing step comprises contacting said sample with a pair of LT1, LT3 or LT4 probes, wherein the members of said pair of LT1, LT3 or LT4 probes hybridize within no more than five nucleotides of each other, wherein a first LT1, LT3 or LT4 probe of said pair of LT1, LT3 or LT4 probes is labelled with a donor fluorescent moiety and said second LT1, LT3 or LT4 probe of said pair of LT1, LT3 or LT4 probes is labelled with a corresponding acceptor fluorescent moiety; and detecting the presence or absence of fluorescence resonance energy transfer (FRET) between said donor fluorescent moiety of said first LT1, LT3 or LT4 probe and said acceptor fluorescent moiety of said second LT1, LT3 or LT4 probe, wherein the presence of FRET is indicative of the presence of bovine transmissible spongiform encephalopathy (BSE) in the mammal from which said sample derives and wherein the absence of FRET is indicative of the absence of BSE in said mammal.

13. The method of claim 12, wherein the LT1 primer pair consists of the oligonucleotides according to SEQ ID NO:2 and SEQ ID NO:3;

the LT3 primer pair consists of the oligonucleotides according to SEQ ID NO:7 and SEQ ID NO:8; and LT4 primer pair consists of the oligonucleotides according to SEQ ID NO:12 and SEQ ID NO:13.

14. The method of claim 12, wherein the pair of LT1 probes consists of the oligonucleotides according to SEQ ID NO:4 and SEQ ID NO:5;

the pair of LT3 probes consists of the oligonucleotides according to SEQ ID NO:9 and SEQ ID NO:10; and the pair of LT4 probes consists of the oligonucleotides according to SEQ ID NO:14 and SEQ ID NO:15.

* * * * *

SEQUENCE LISTING

```
<160> NUMBER OF SEQ ID NOS: 15

<210> SEQ ID NO 1
<211> LENGTH: 230
<212> TYPE: DNA
<213> ORGANISM: Bos taurus
<220> FEATURE:
<221> NAME/KEY: misc_feature
<223> OTHER INFORMATION: LT1

<400> SEQUENCE: 1
ccttgagaag cgttatgtgg ggaggtatct gtcacccacg cagaaatgct tctgacaggc      60
ggcacatttg aaacattcca ggtgatacac tttgtccttc acccgcatcg tcatctcgta     120
ggcacggatc cgcttgtcac aggatgcaca gagaccatct tggccgaaaa gcctgaggta     180
gtctcggcgg cagagcttcc ggcccagctt gtagtagagg cgccggccca                230
```

```
<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      LT1 oligonucleotide primer, forward orientation

<400> SEQUENCE: 2
ggcggcacat ttgaaac                                                  17

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      LT1 oligonucleotide primer, reverse orientation

<400> SEQUENCE: 3
ctctactaca agctgggc                                                 18

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      LT1 detection probe

<400> SEQUENCE: 4
gtgatacact ttgtccttca cccg                                          24

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      LT1 detection probe

<400> SEQUENCE: 5
tcgtcatctc gtaggcacgg                                               20

<210> SEQ ID NO 6
<211> LENGTH: 325
<212> TYPE: DNA
<213> ORGANISM: Bos taurus
<220> FEATURE:
<221> NAME/KEY: misc_feature
<223> OTHER INFORMATION: LT3

<400> SEQUENCE: 6
gagacatttg gccaaaagag gaatttccag gacaccaaca acatccatta ttccattatt    60
catttgtttc ctgaagagca aacacttcct tgaaattctt ctcaaattct gcctccagtc   120
taagccccat ttggccaaaa tcattgaact tgaaagatgc cctgtggttc tgaaagatga   180
gacgcatgtc ccacacaaac ccttccacat tggagtagcc ctgctcattc agcctcttct   240
tgatcttgtc cagccacatg ggctccttga ggttttaga agcctctttc atataataat    300
aatagggaat cctcactata acgct                                        325

<210> SEQ ID NO 7
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      LT3 oligonucleotide primer, forward orientation

<400> SEQUENCE: 7
gacaccaaca acatccatta t                                              21

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      LT3 oligonucleotide primer, reverse orientation

<400> SEQUENCE: 8
aacctcaagg agccca                                                    16

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      LT3 detection probe

<400> SEQUENCE: 9
gtggttctga aagatgagac gca                                            23

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      LT3 detection probe

<400> SEQUENCE: 10
tcccacacaa acccttccac                                                20

<210> SEQ ID NO 11
<211> LENGTH: 472
<212> TYPE: DNA
<213> ORGANISM: Bos taurus
<220> FEATURE:
<221> NAME/KEY: misc_feature
<223> OTHER INFORMATION: LT4

<400> SEQUENCE: 11
tctgcagaat tcgcctttga gaagcgttat gggggcgagg tggtaaagga agcttacaaa    60
acaactattc tttaaaaaaa aacaaaaaaa caaaaaaaca aaaacagca aaagccaacc    120 ggcccaattt tgtctccagt tttcaacgtg tgctttcgag catttcagct gtttccagtt   180
actttagttt ccagatatta gtcttccatt tagttttaag actaaatctc acttttggat   240
aaacacaagg aaatattta cttgctgaaa aatcacttta ctggataaag ttacctctta    300
tgcctttcag ttttctaatc caactttctg acaaccagtg gtaattagga agttctaagt   360
tgcagttgtc cctatgactt tgggcttccc tggtggctca gctggtcaaa aatctgcctg   420
caatgcggga gacctccacc ccataacgct tctcaaaggc gaattctgca ga          472

<210> SEQ ID NO 12
<211> LENGTH: 17
<212> TYPE: DNA
<213> ORGANISM: Artificial Sequence
```

-continued

```
<220> FEATURE:
<223> OTHER INFORMATION: Description of Artificial Sequence: Synthetic
      LT4 oligonucleotide primer, forward orientation

<400> SEQUENCE: 12
ttcaacgtgt gctttcg                                                  17

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      LT4 oligonucleotide primer, reverse orientation

<400> SEQUENCE: 13
accagggaag cccaaa                                                   16

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      LT4 detection probe

<400> SEQUENCE: 14
agttacctct tatgcctttc agttttct                                      28

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      LT4 detection probe

<400> SEQUENCE: 15
tccaactttc tgacaaccag tggt                                          24
```